(12) United States Patent
Chiou et al.

(10) Patent No.: US 7,767,441 B2
(45) Date of Patent: Aug. 3, 2010

(54) BIOASSAY SYSTEM INCLUDING OPTICAL DETECTION APPARATUSES, AND METHOD FOR DETECTING BIOMOLECULES

(75) Inventors: Chung-Fan Chiou, Cyonglin Township, Hsinchu County (TW); Cheng-Wei Chu, Yonghe (TW); Shang-Chia Chang, Zhubei (TW); Yu-Tang Li, Tucheng (TW); Chao-Chi Pan, Hsinchu (TW); Bin-Cheng Yao, Taipei (TW)

(73) Assignee: Industrial Technology Research Institute, Jhudong Township, Hsinchu County (TW)

( * ) Notice: Subject to any disclaimer, the term of this patent is extended or adjusted under 35 U.S.C. 154(b) by 18 days.

(21) Appl. No.: 12/255,044

(22) Filed: Oct. 21, 2008

(65) Prior Publication Data

US 2009/0146076 A1    Jun. 11, 2009

Related U.S. Application Data

(60) Provisional application No. 60/996,016, filed on Oct. 25, 2007, provisional application No. 61/036,652, filed on Mar. 14, 2008.

(51) Int. Cl.
*C12M 3/00* (2006.01)
(52) U.S. Cl. ................................ 435/287.2
(58) Field of Classification Search .................. None
See application file for complete search history.

(56) References Cited

U.S. PATENT DOCUMENTS

| | | | |
|---|---|---|---|
| 4,748,111 A | 5/1988 | Dattagupta et al. | |
| 4,942,124 A | 7/1990 | Church | |
| 5,149,625 A | 9/1992 | Church et al. | |
| 5,302,509 A | 4/1994 | Cheeseman | |
| 5,547,859 A | 8/1996 | Goodman et al. | |
| 5,653,939 A | 8/1997 | Hollis et al. | |
| 5,700,637 A | 12/1997 | Southern | |
| 5,741,644 A | 4/1998 | Kambara et al. | |
| 5,744,305 A | 4/1998 | Fodor et al. | |
| 5,750,341 A | 5/1998 | Macevicz | |
| 5,753,788 A | 5/1998 | Fodor et al. | |
| 5,755,943 A | 5/1998 | Middendorf et al. | |
| 5,789,168 A | 8/1998 | Leushner et al. | |
| 5,795,722 A | 8/1998 | Lacroix et al. | |
| 5,843,767 A * | 12/1998 | Beattie ................ 435/287.1 | |
| 5,928,919 A | 7/1999 | Reha-Krantz et al. | |
| 5,945,283 A | 8/1999 | Kwok et al. | |
| 5,945,284 A | 8/1999 | Livak et al. | |
| 5,945,312 A | 8/1999 | Goodman et al. | |
| 5,952,174 A | 9/1999 | Nikiforov et al. | |
| 5,954,932 A | 9/1999 | Takahashi et al. | |
| 5,965,446 A | 10/1999 | Ishikawa | |
| 5,968,740 A | 10/1999 | Fodor et al. | |
| 5,974,164 A | 10/1999 | Chee | |
| 5,976,338 A | 11/1999 | Fujita et al. | |
| 5,981,186 A | 11/1999 | Gabe et al. | |
| 5,994,058 A | 11/1999 | Senapathy | |
| 6,013,434 A | 1/2000 | Tregear et al. | |
| 6,017,702 A | 1/2000 | Lee et al. | |
| 6,018,041 A | 1/2000 | Drmanac et al. | |
| 6,043,080 A | 3/2000 | Lipshutz et al. | |
| 6,046,005 A | 4/2000 | Ju et al. | |
| 6,049,380 A | 4/2000 | Goodwin et al. | |
| 6,051,380 A | 4/2000 | Sosnowski et al. | |
| 6,153,737 A | 11/2000 | Manoharan et al. | |
| 6,197,513 B1 | 3/2001 | Coull et al. | |
| 6,261,782 B1 | 7/2001 | Lizardi et al. | |
| 6,413,722 B1 | 7/2002 | Arnold et al. | |
| 6,511,803 B1 | 1/2003 | Church et al. | |
| 6,524,829 B1 | 2/2003 | Seeger | |
| 6,537,749 B2 | 3/2003 | Kuimelis et al. | |
| 6,613,523 B2 | 9/2003 | Fischer | |
| 6,692,915 B1 | 2/2004 | Nallur | |

(Continued)

FOREIGN PATENT DOCUMENTS

| | | |
|---|---|---|
| CN | 1690690 A | 11/2005 |
| DE | 102004015272 A1 | 11/2005 |
| WO | WO 2006/083751 | 8/2006 |

OTHER PUBLICATIONS

Celine Adessi et al., "Solid phase DNA amplification: characterization of primer attachment and amplication mechanisms," Nucleic Acids Research, vol. 28, No. 20, e87 (2000).

(Continued)

*Primary Examiner*—Ann Y Lam
(74) *Attorney, Agent, or Firm*—Finnegan, Henderson, Farabow, Garrett & Dunner, L.L.P.

(57) ABSTRACT

A bioassay system is disclosed. The bioassay system may include a plurality of optical detection apparatuses, each of which includes a substrate having a light detector, and a linker site formed over the light detector, the linker site being treated to affix the biomolecule to the linker site. The linker site is proximate to the light detector and is spaced apart from the light detector by a distance of less than or equal to 100 micrometers. The light detector collects light emitted from the biomolecule within a solid angle of greater than or equal to 0.8 SI steridian. The optical detection apparatus may further include an excitation light source formed over the substrate so as to provide a light source for exciting a fluorophore attached to the biomolecule.

58 Claims, 6 Drawing Sheets

U.S. PATENT DOCUMENTS

| | | |
|---|---|---|
| 6,750,016 B2 | 6/2004 | Mirkin et al. |
| 6,770,441 B2 | 8/2004 | Dickinson et al. |
| 6,787,308 B2 | 9/2004 | Balasubramanian et al. |
| 6,833,246 B2 | 12/2004 | Balasubramanian |
| 6,858,394 B1 | 2/2005 | Chee et al. |
| 6,946,249 B2 | 9/2005 | Head et al. |
| 7,057,026 B2 | 6/2006 | Barnes et al. |
| 7,094,531 B1 | 8/2006 | Schmidt et al. |
| 7,115,400 B1 | 10/2006 | Adessi et al. |
| 7,133,782 B2 | 11/2006 | Odedra |
| 7,169,560 B2 | 1/2007 | Lapidus et al. |
| 7,211,390 B2 | 5/2007 | Rothberg et al. |
| 7,220,549 B2 | 5/2007 | Buzby |
| 7,226,734 B2 | 6/2007 | Chee et al. |
| 7,232,656 B2 | 6/2007 | Balasubramanian et al. |
| 7,264,929 B2 | 9/2007 | Rothberg et al. |
| 7,361,466 B2 | 4/2008 | Korlach et al. |
| 2002/0094533 A1* | 7/2002 | Hess et al. ............ 435/6 |
| 2003/0059820 A1 | 3/2003 | Vo-Dinh |
| 2004/0249227 A1 | 12/2004 | Klapproth et al. |
| 2005/0266456 A1 | 12/2005 | Williams et al. |
| 2005/0287523 A1* | 12/2005 | Letant et al. ............ 435/5 |
| 2006/0021666 A1* | 2/2006 | Funatsu et al. ............ 137/828 |
| 2007/0141598 A1 | 6/2007 | Turner et al. |
| 2008/0081769 A1 | 4/2008 | Hassibi |
| 2008/0199932 A1 | 8/2008 | Hanzel et al. |

OTHER PUBLICATIONS

Timothy D. Harris et al., "Single-Molecule DNA Sequencing of a Viral Genome," Science, 320, 106 (2008).

Timothy D. Harris et al., On-Line Supplement for "Single-Molecule DNA Sequencing of a Viral Genome," Science, 320, 106 (2008), pp. 1-25.

Jingyue Ju et al., "Four-color DNA sequencing by synthesis using cleavable fluorescent nucleotide reversible terminators," PNAS, vol. 103, No. 52, pp. 19635-19640 (2006).

Emil P. Kartalov et al., "Microfluidic device reads up to four consecutive base pairs in DNA sequencing-by-synthesis," Nucleic Acids Research, vol. 32, No. 9, pp. 2873-2879 (2004).

Jonas Korlach et al., "Selective aluminum passivation for targeted immobilization of single DNA polymerase molecules in zero-mode waveguide nanostructures," PNAS, vol. 105, No. 4, pp. 1176-1181 (2008).

Joshua D. Levin, "Position-dependent effects of locked nucleic acid (LNA) on DNA sequencing and PCR primers," Nucleic Acids Research, vol. 34, No. 20, e142 (2006).

PCT International Search Report and Written Opinion mailed Feb. 12, 2009, in related International Application No. PCT/CN2008/072824.

* cited by examiner

| Layer # | Material | Thickness (nm) | Layer # | Material | Thickness (nm) |
|---|---|---|---|---|---|
| 1 | $Nb_2O_5$ | 20.56 | 51 | $Nb_2O_5$ | 63.08 |
| 2 | $SiO_2$ | 108.04 | 52 | $SiO_2$ | 93.75 |
| 3 | $Nb_2O_5$ | 48.03 | 53 | $Nb_2O_5$ | 63.66 |
| 4 | $SiO_2$ | 92.18 | 54 | $SiO_2$ | 89.79 |
| 5 | $Nb_2O_5$ | 61.85 | 55 | $Nb_2O_5$ | 58.99 |
| 6 | $SiO_2$ | 89.03 | 56 | $SiO_2$ | 93.83 |
| 7 | $Nb_2O_5$ | 61.52 | 57 | $Nb_2O_5$ | 58.88 |
| 8 | $SiO_2$ | 91.91 | 58 | $SiO_2$ | 91.3 |
| 9 | $Nb_2O_5$ | 63.12 | 59 | $Nb_2O_5$ | 58.66 |
| 10 | $SiO_2$ | 97 | 60 | $SiO_2$ | 90.59 |
| 11 | $Nb_2O_5$ | 57 | 61 | $Nb_2O_5$ | 58.58 |
| 12 | $SiO_2$ | 102.89 | 62 | $SiO_2$ | 92.95 |
| 13 | $Nb_2O_5$ | 59.97 | 63 | $Nb_2O_5$ | 60.41 |
| 14 | $SiO_2$ | 98.2 | 64 | $SiO_2$ | 90.7 |
| 15 | $Nb_2O_5$ | 62.48 | 65 | $Nb_2O_5$ | 60.45 |
| 16 | $SiO_2$ | 87.65 | 66 | $SiO_2$ | 94.23 |
| 17 | $Nb_2O_5$ | 65.9 | 67 | $Nb_2O_5$ | 62.64 |
| 18 | $SiO_2$ | 101.19 | 68 | $SiO_2$ | 92.88 |
| 19 | $Nb_2O_5$ | 58.79 | 69 | $Nb_2O_5$ | 59.57 |
| 20 | $SiO_2$ | 95.53 | 70 | $SiO_2$ | 95.27 |
| 21 | $Nb_2O_5$ | 64.05 | 71 | $Nb_2O_5$ | 66.51 |
| 22 | $SiO_2$ | 93.45 | 72 | $SiO_2$ | 90.96 |
| 23 | $Nb_2O_5$ | 62.36 | 73 | $Nb_2O_5$ | 59.86 |
| 24 | $SiO_2$ | 97.28 | 74 | $SiO_2$ | 102.27 |
| 25 | $Nb_2O_5$ | 62.53 | 75 | $Nb_2O_5$ | 60.21 |
| 26 | $SiO_2$ | 86.22 | 76 | $SiO_2$ | 96.68 |
| 27 | $Nb_2O_5$ | 57.06 | 77 | $Nb_2O_5$ | 62.96 |
| 28 | $SiO_2$ | 111.55 | 78 | $SiO_2$ | 94.71 |
| 29 | $Nb_2O_5$ | 41.78 | 79 | $Nb_2O_5$ | 60.58 |
| 30 | $SiO_2$ | 40.22 | 80 | $SiO_2$ | 95.43 |
| 31 | $Nb_2O_5$ | 109.42 | 81 | $Nb_2O_5$ | 64.27 |
| 32 | $SiO_2$ | 14.85 | 82 | $SiO_2$ | 100.1 |
| 33 | $Nb_2O_5$ | 49.18 | 83 | $Nb_2O_5$ | 60.13 |
| 34 | $SiO_2$ | 118.53 | 84 | $SiO_2$ | 90.33 |
| 35 | $Nb_2O_5$ | 44.43 | 85 | $Nb_2O_5$ | 66.04 |
| 36 | $SiO_2$ | 87.33 | 86 | $SiO_2$ | 97.31 |
| 37 | $Nb_2O_5$ | 61.55 | 87 | $Nb_2O_5$ | 60.99 |
| 38 | $SiO_2$ | 109.86 | 88 | $SiO_2$ | 90.95 |
| 39 | $Nb_2O_5$ | 60.33 | 89 | $Nb_2O_5$ | 62.41 |
| 40 | $SiO_2$ | 86.57 | 90 | $SiO_2$ | 100.72 |
| 41 | $Nb_2O_5$ | 62.75 | 91 | $Nb_2O_5$ | 65.12 |
| 42 | $SiO_2$ | 104.16 | 92 | $SiO_2$ | 86.45 |
| 43 | $Nb_2O_5$ | 61.44 | 93 | $Nb_2O_5$ | 59.12 |
| 44 | $SiO_2$ | 94.26 | 94 | $SiO_2$ | 99.52 |
| 45 | $Nb_2O_5$ | 60.92 | 95 | $Nb_2O_5$ | 66.74 |
| 46 | $SiO_2$ | 95.65 | 96 | $SiO_2$ | 86.2 |
| 47 | $Nb_2O_5$ | 61.81 | 97 | $Nb_2O_5$ | 53.98 |
| 48 | $SiO_2$ | 98.2 | 98 | $SiO_2$ | 96.6 |
| 49 | $Nb_2O_5$ | 60.24 | 99 | $Nb_2O_5$ | 67.27 |
| 50 | $SiO_2$ | 92.2 | 100 | $SiO_2$ | 107.09 |
|  |  |  | 101 | $Nb_2O_5$ | 20.2 |

Fig. 5

BIOASSAY SYSTEM INCLUDING OPTICAL DETECTION APPARATUSES, AND METHOD FOR DETECTING BIOMOLECULES

RELATED APPLICATIONS

This application claims the benefit of priority to U.S. Provisional Patent Application No. 60/996,016, filed Oct. 25, 2007, and U.S. Provisional Patent Application No. 61/036,652, filed Mar. 14, 2008, the entire contents of both of which are incorporated by reference herein in their entirety.

TECHNICAL FIELD

The present invention relates to a bioassay system including a plurality of optical detection apparatuses, and uses of the bioassay system for detecting and analyzing biomolecules, such as nucleic acids. More particularly, the present invention relates to a bioassay system including at least ten thousand optical detection apparatuses for monitoring, in some embodiments, a large number of fluorophore molecules in parallel for detecting and analyzing the biomolecules.

BACKGROUND

The Human Genome Project (HGP) spurred a great increase in sequencing throughput and resulted in a corresponding drop in sequencing costs. In contrast to the 13 years and cost of nearly three billion US dollars, per genome sequencing costs have been reduced significantly—indeed two individual genomes have recently been completed (McGuire et al., *Science* 317:1687 (2007)). Personal genomes represent a paradigm shift in medical treatment for both patients and health care providers. By managing genetic risk factors for disease, health care providers can more readily practice preventative medicine and provide customized treatment. With large banks of completed genomes, drug design and administration can be more efficient, pushing forward the nascent field of pharmacogenomics.

To popularize customized medical treatment for individuals, the US National Institutes of Health (NIH) National Human Genome Research Institute (NHGRI) set a benchmark of reducing per-genome sequencing costs from ten million to approximately one thousand U.S. dollars. Conventional high-throughput capillary electrophoresis and automated genome sequencing technology, however, cannot satisfy the increased demand for individual genome sequencing. In addition, existing sequencing methods require complicated and error-prone image acquisition and analysis steps. For example, many existing technologies require either the array or detection system to move in order to capture multiple images. The resulting images must then be tiled, aligned, and analyzed. Image acquisition, processing, and analysis steps are all prone to errors, take additional time, and require expensive equipment. Conversely, existing systems that do not involve moving optics, are typically limited by a very modest number of detecting units. Finally, existing devices do not place the molecule being detected in close proximity to a corresponding detecting unit, which substantially limits the strength of the detected signal.

Accordingly, a need exists for devices to reduce the cost of nucleic acid sequencing. To approach the "$1000 genome" paradigm, devices should be capable of sequencing multiple molecules in parallel, have simplified design and manufacture processes, and avoid the need of existing devices and methods for complicated and error-prone scanning and image analysis processes. Additionally, the devices should be capable of sequencing single molecules to avoid the known difficulty of asynchrony in both the amplification (e.g., drift between the sequences of ideally clonal templates) and sequencing (e.g., dephasing of the stepwise sequencing reactions amongst the sequencing templates) steps of clustered sequencing methods.

SUMMARY

The present invention provides a bioassay system including a plurality of optical detection apparatuses, and methods of using the bioassay system for nucleic acid detection, e.g., sequencing. The bioassay system provided by the invention is capable of large-scale parallel sequencing reactions, i.e., simultaneously sequencing a large number of different nucleic acid templates. Each sequencing reaction uses a single molecule as the template (i.e., single molecule sequencing). The devices provided also have simplified designs—obviating the need of current devices for complicated, expensive, and error-prone scanning and detection steps. The simplified design and function of the system provided by the invention is based, in part, on the direct correspondence of linker sites to which the nucleic acids being detected are attached (either directly, or, e.g., by a polymerase molecule) and one or more detecting units (e.g., light detectors), and in part, on the short distance between the linker sites and the detecting units. This short distance between the nucleic acid and detecting unit is manifested, in some embodiments, by a large solid angle of detection.

In one aspect, there is provided a bioassay system for identifying a single biomolecule at a detecting unit. The bioassay system may include a plurality of optical detection apparatuses, each of which comprises a substrate having a light detector, and a linker site formed over the light detector, the linker site being treated to affix the biomolecule to the linker site, wherein the linker site is proximate to the light detector. In some embodiments, the linker site is spaced apart from the light detector by a distance of less than or equal to 100 micrometers, and the light detector collects light emitted from the biomolecule within a solid angle of greater than or equal to 0.8 SI steridian. The optical detection apparatus may further include an excitation light source formed over the substrate so as to provide a light source for exciting a fluorophore attached to the biomolecule.

In another aspect, the invention provides a method of detecting a nucleic acid by linking at least one nucleic acid to a linker site of an optical detection apparatus provided by the invention (either directly or by binding a nucleic acid polymerase bound to the linker site) and detecting the nucleic acid on a corresponding light detector. In some embodiments, the nucleic acid is detected by hybridization, e.g., to a labeled probe. In some embodiments the nucleic acid is detected by performing nucleic acid sequencing on the optical detection apparatus. In some embodiments, the nucleic acid sequencing method is chosen from base-extension sequencing, terminally-labeled phosphate sequencing, and wobble sequencing. In particular embodiments, the sequencing reaction is a base-extension sequencing reaction. In still more particular embodiments, the base-extension sequencing reaction further comprises the step of adding blocked and labeled nucleotides to the optical detection apparatus. In yet more particular embodiments, the nucleotides are fluorescently labeled.

The invention also provides, in another aspect, methods of detecting a sample molecule. In some embodiments, these methods include the steps of affixing a labeled sample molecule to a linker site on an optical detection apparatus provided by the invention and detecting the sample molecule on a corresponding light detector. In some embodiments, the sample molecule is affixed to a linker site by a linking molecule. In some embodiments the linking molecule comprises 1) a capture molecule suitable for binding the sample molecule and 2) a nucleic acid tag. In particular embodiments, the sample molecule is applied to an optical detection apparatus provided by the invention, to which linking molecules have already been affixed to linker sites. In other embodiments, a sample molecule is allowed to bind a linking molecule and the bound complex is then applied to the optical detection apparatus and allowed to affix to a linker site. In particular embodiments, the sample molecule is a biomolecule, e.g., a polypeptide, nucleic acid, lipid, polysaccharide, or metabolite.

It is to be understood that both the foregoing general description and the following detailed description are exemplary and explanatory only, and are not restrictive of the claimed invention.

BRIEF DESCRIPTION OF THE DRAWINGS

FIG. 5 is a table illustrating the construction of a filter layer in accordance with an embodiment consistent with the present invention.

DETAILED DESCRIPTION

Figure 1:
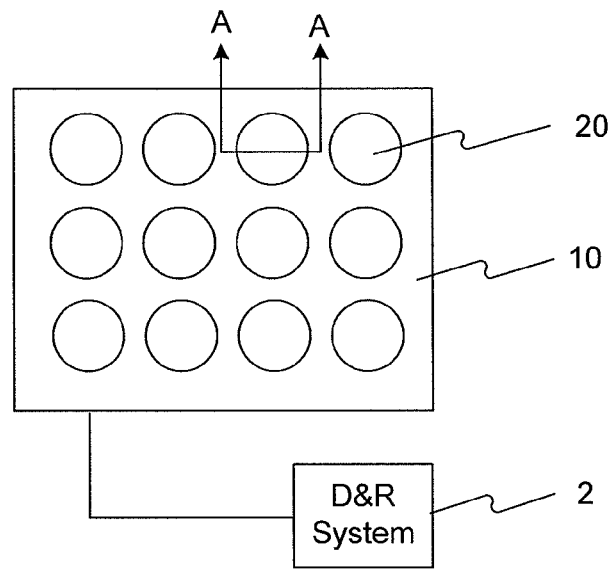
FIG. 1 is a plane view illustrating a bioassay system including an array of optical detection apparatuses consistent with the present invention.

Reference will now be made in detail to embodiments consistent with the present invention, examples of which are illustrated in the accompanying drawings. Wherever possible, same reference numerals will be used throughout the drawings to refer to same or like parts.

1. Bioassay System

The bioassay system consistent with the present invention can be used to monitor a large number (e.g., in some embodiments, more than 10,000) of single biomolecules in parallel. The bioassay system may include a plurality of optical detection apparatuses. Each optical detection apparatus may sense the existence of a fluorophore on the single molecule by detecting photons emitted from the fluorophore. By operating the optical detection apparatuses in parallel, the bioassay system consistent with the present invention may determine, for example, the sequence of a genome or the profile of expressed genes in a tissue sample with high throughput.

Referring to FIG. 1, a bioassay system 1 consistent with the present invention is illustrated. Bioassay system 1 may include a bioassay substrate 10 and a plurality of optical detection apparatuses 20 formed on substrate 10. Each optical detection apparatus 20 may be operated independently to detect and identify a single biomolecule affixed thereto. For example, the sequence of a single stranded DNA may be determined by sequentially performing a base extension and detecting light emitted from a fluorophore coupled with the extended base using optical detection apparatus 20. By integrating a huge number of optical detection apparatuses 20 on substrate 10, a huge number of single biomolecules can be detected and identified in parallel. Depending on design choices, bioassay system 1 may include at least, for example, ten-thousand (10,000), two-hundred-fifty-thousand (250,000), two-million (2,000,000), or even ten-million (10,000,000), or more, optical detection apparatuses 20 formed on substrate 10.

Bioassay system 1 may further include a detection and recordation system 2 coupled with substrate 10 for controlling the operation of optical detection apparatuses 20 and for recording data acquired from optical detection apparatuses 20. In addition, bioassay system 1 may further include an excitation light source (not shown). The excitation light source may produce excitation light, so as to induce the fluorophore to emit fluorescent light. In one embodiment, the excitation light source may be stand alone from optical detection apparatuses 20 or bioassay substrate 10. In alternative embodiments, the excitation light source may be integrated with optical detection apparatuses 20 or bioassay substrate 10.

In this particular embodiment, as shown in FIG. 1, optical detection apparatus 20 may have a circular shape when viewed from above. It is to be understood that optical detection apparatus 20 may have other geometrical shapes, such as a square shape, a polygon shape, an oval shape, and the like. In addition, FIG. 1 shows that the plurality of optical detection apparatuses 20 is arrayed in a square lattice pattern. It is to be understood that optical detection apparatuses 20 may be arrayed in other patterns, such as a triangular lattice pattern, a honeycomb lattice pattern, and the like.

Because the plurality of optical detection apparatuses 20 of bioassay system 1 are independently operable, only one optical detection apparatus 20 will be described below in accordance with various embodiments consistent with the present invention. Although only one optical detection apparatus 20 will be described, it is appreciated that different optical detection apparatuses 10 in bioassay system 1 are not necessarily the same. Depending on design choices, different types of optical detection apparatuses 20 may be constructed according to different embodiments consistent with the present invention.

Figure 2:
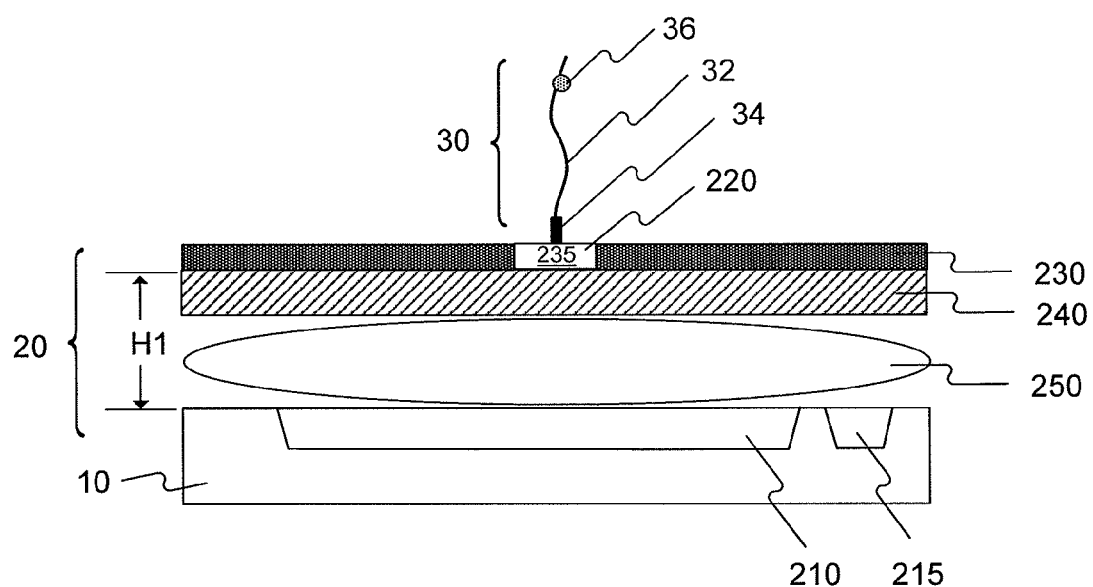
FIG. 2 is a sectional view, along line A-A of FIG. 1, illustrating an optical detection apparatus in accordance with an embodiment consistent with the present invention.

Referring to FIG. 2, there is illustrated a section view, along line A-A of FIG. 1, of an optical detection apparatus 20 in accordance with one embodiment consistent with the present invention. As shown in FIG. 2, optical detection apparatus 20 includes a light detector 210 formed on substrate 10, and a linker site 220 formed over light detector 210. In addition, optical detection apparatus 20 may further include a control circuit 215 formed on substrate 10 for controlling the operation of light detector 210. Control circuit 215 may be coupled with detection and recordation system 2 so as to receive control instructions from detection and recordation system 2 and to transmit detected signals to detection and recordation system 2. In some embodiments, substrate 10 may be a glass substrate, a semiconductor substrate (e.g., silicon), or a plastics substrate. In some embodiments, one or more control circuits 215 may correspond to each light detector 210.

In some embodiments, light detector 210 may comprise a single photoconductive photon detector or a group of photoconductive photon detectors. In alternative embodiments, light detector 210 may comprise a single photovoltaic photon detector or a group of photovoltaic photon detectors. In alternative embodiments, light detector 210 may comprise a single photodiode or a group of photodiodes. In alternative embodiments, light detector 210 may comprise a single avalanche photodiode or a group of avalanche photodiodes. In alternative embodiments, light detector 210 may comprise a single phototransistor or a group of phototransistors.

In one embodiment, optical detection apparatus 20 may further include a blind sheet 230 over light detector 210. Blind sheet 230 may include a pinhole 235. In one embodiment, pinhole 235 may have a circular shape and may have a diameter D1 of less than or equal to 1,000, 500, 300, 200, 150, or 100 nanometers. It is appreciated that pinhole 235 may have other shapes, such as an oval shape, a square shape, and the like. In one embodiment, blind sheet 230 may comprise an opaque material, so as to block away undesired light from reaching light detector 210. Therefore, desired light may reach light detector 210 via pinhole 235.

Linker site 220 may be formed proximate to pinhole 235. In the embodiment illustrated in this figure, linker site 220 is formed inside of pinhole 235. In one embodiment, linker site 220 formed proximate to pinhole 235 may be spaced apart from light detector 210 by a distance H1 of less than or equal to 100 micrometers. In alternative embodiments, distance H1 may be less than or equal to 75, 50, 25, 15, 10, 5, or 3 micrometers.

Optical detection apparatus 20 may further include a filter layer 240 (optional) and a microlens 250 (optional) between light detector 210 and blind sheet 230. Although FIG. 2 shows filter layer 240 is formed over microlens 250, it is appreciated that filter layer 240 may be formed under microlens 250. In some embodiments, filter layer 240 may include a single transparent layer, or a plurality of transparent sublayers having different refractive indices. When filter layer 240 includes a plurality of sublayers, filter layer 240 may be formed by sequentially depositing the sublayers over substrate 10. In some embodiments, a sublayer having a higher refractive index may be sandwiched by two sublayers having lower refractive indices. Alternatively, a sublayer having a lower refractive index may be sandwiched by two sublayers having higher refractive indices. In some embodiments, filter layer 240 may include a layer with single region, or a layer with a plurality of sub-regions having different transparency to different wavelength ranges.

Referring still to FIG. 2, linker site 220 may be treated to affix a single biomolecule 30 thereto. In one embodiment, biomolecule 30 may include a single stranded DNA molecule 32 and an end link primer 34 coupled with DNA molecule 32. Biomolecule 30 may be affixed to linker site 220 via end link primer 34. Further, DNA molecule 32 may be labeled with a fluorophore 36. When excited by excitation light of a first wavelength $\lambda 1$, fluorophore 36 may emit fluorescent light of a second wavelength $\lambda 2$. In some embodiments, first wavelength $\lambda 1$ is shorter than second wavelength $\lambda 2$. In some embodiments, first wavelength $\lambda 1$ is longer than second wavelength $\lambda 2$, e.g., in multi-photon excitation. Light detector 210 then detects the fluorescent light emitted from fluorophore 36, so as to identify the type of base that fluorophore 36 is attached to, thereby sequentially determining the sequence of DNA molecule 32.

Figure 3:
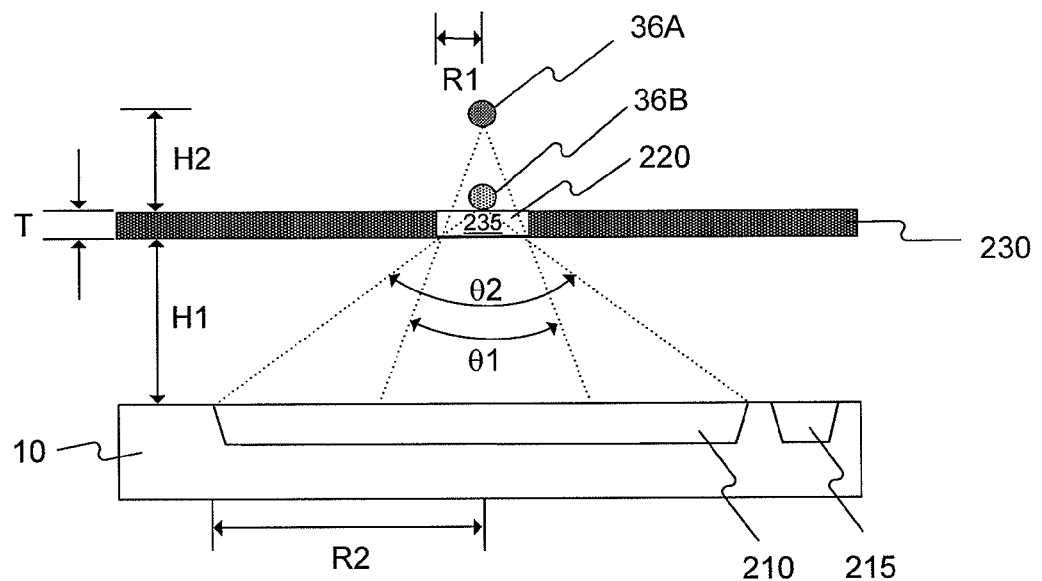
FIG. 3 is a sectional view illustrating dimension details of the optical detection apparatus consistent with the present invention.

Referring to FIG. 3, there is illustrated a sectional view of optical detection apparatus 20 in accordance with one embodiment consistent with the present invention. As shown in FIG. 3, blind sheet 230 is formed over light detector 210 and vertically spaced apart from light detector 210 by distance H1. Blind sheet 230, which has a thickness T, includes pinhole 235 having a radius R1 (i.e., one-half of diameter D1). In this embodiment, linker site 220 may be formed in pinhole 235 to bind with a biomolecule (not shown).

When fluorophore 36 is found at a first location 36A above linker site 220 and separate from linker site 220 by a distance H2, light detector 210 having a radius R2 may collect fluorescent light emitted from fluorophore 36 within a first solid angle $\theta 1$. When fluorophore 36 is found at a second location 36B and almost contacts linker site 220 (i.e., distance H2 approaches zero or less than 1 micrometer), light detector 210 may then collect fluorescent light emitted from fluorophore 36 within a second solid angle $\theta 2$. Second solid angle $\theta 2$ is greater than first solid angle $\theta 1$, and provides a substantially stronger signal.

In order for light detector 210 to be exposed to the fluorescent light emitted from fluorophore 36 through pinhole 235, radius R2 of light detector 210 must be greater than or equal to the radius that corresponds to second solid angle $\theta 2$ projected on an upper surface of light detector 210. By bringing blind sheet 230 (or linker site 220) closer to light detector 210 (i.e., by decreasing distance H1), light detector 210 may then collect more concentrated light (i.e., a stronger light signal) from within a solid angle. In one embodiment, blind sheet 230 (or linker site 220) and light detector 210 are separated by a small distance H1, such that second solid angle $\theta 2$ is at least 0.8 SI steridian.

Figure 4:
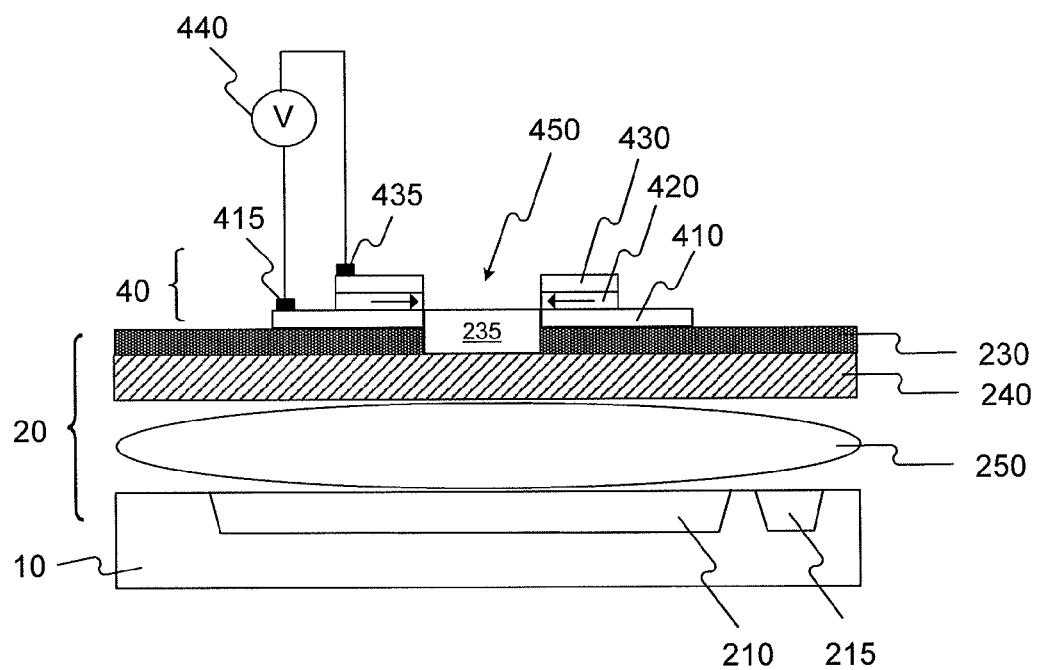
FIG. 4 is a sectional view, along line A-A of FIG. 1, illustrating an optical detection apparatus in accordance with another embodiment consistent with the present invention.

Referring to FIG. 4, there is illustrated a section view, along line A-A of FIG. 1, of optical detection apparatus 20 in accordance with another embodiment consistent with the present invention. In this embodiment, an excitation light source 40 is integrated with optical detection apparatus 20. As shown in FIG. 4, excitation light source 40 is formed on blind sheet 230 of optical detection apparatus 20. In one embodiment, excitation light source 40 may comprise a p-type and a n-type semiconductor layers (410 and 430), and a light emitting layer 420 between the junction region of layer 410 and layer 430. Layer 410 and layer 430 may be connected to a power source. Depending on the materials and/or the materials' physical and atomic structure used for layers 410, 420, and 430, excitation light source 40 may be a light emitting diode (LED), a light emitting laser diode (LD), an organic light emitting diode (OLED), or a polymer light emitting diode (PLED). Inorganic materials, such as gallium arsenide, indium phosphide, gallium antimonide, and gallium nitride, or organic materials, such as conjugated polymers with a poly(para-phenelyene-vinylene) backbone are all examples of semiconductor materials that can be used to create junction diodes that emit light.

In other embodiments, excitation light source 40 may form blind sheet 230 or may be formed within blind sheet 230. In some embodiments, excitation light source 40 integrated with optical detection apparatus 20 may emit light of one wavelength band or a plurality of wavelength bands. Excitation light source 40 may emit light intermittently or continuously. Excitation light source 40 may emit light of one wavelength band at a time or several wavelength bands simultaneously.

Referring again to FIG. 4, excitation light source 40 may include a cavity 450 at a central portion thereof, so as to expose pinhole 235. In this embodiment, linker site 220 may not be formed in pinhole 235. Rather, linker site 220 may be formed in cavity 450 and proximate to pinhole 235. In the embodiments where excitation light source 40 forms blind sheet 230 or is formed within blind sheet 230, cavity 450 forms pinhole 235 or is formed within pinhole 235. In some embodiments, pinhole 235 may be formed at a central portion of both layer 410 and blind sheet 230 by, for example, etching layer 410 and blind sheet 230 using an appropriate process.

In addition, excitation light source 40 may be coupled with a power source 440 through a metal contact 415 formed on lower layer 410 and a metal contact 435 formed on upper layer 430. Power source 440 may be stand alone and be controlled by detection and recordation system 2, or may be integrated with detection and recordation system 2.

Light emitting layer 420 of excitation light source 40 may emit excitation light into cavity 450 along a horizontal direction as indicated by arrows drawn on light emitting layer 420 in FIG. 4. In this embodiment, excitation light is emitted along a direction substantially parallel to an upper surface of blind sheet 230. Accordingly, excitation light may not interfere with the fluorescent light that reaches light detector 210. Optical detection apparatus 20 consistent with the present invention may thus more accurately identify biomolecules than conventional devices.

2. Nucleic Acid Detection

The bioassay system consistent with the present invention (including, e.g., either a single optical detection apparatus, or a plurality of such apparatuses) can be used as part of a system for or in methods or processes of molecule detection, e.g., nucleic acid sequencing. This bioassay system, and methods or processes utilizing it, is useful for, e.g., analytical and diagnostic applications. These applications may be private, public, commercial, or industrial.

In some embodiments, the bioassay system is suitable for large-scale parallel sequencing of nucleic acids. Due, in part, to the direct correspondence of linker sites and light detectors of the bioassay system, and/or the close proximity of linker sites and light detectors (manifested, in some embodiments, as a large solid angle), the bioassay system provided in the present invention can be used to sequence nucleic acids without the need for expensive, complicated, and error-prone scanning and analysis systems, e.g., a moving scanning lens or a moving device stage and subsequent image analysis, thus reducing errors and costs. The bioassay system can detect light signals with substantially improved signal strength, which makes single molecule analysis possible.

The bioassay system consistent with the present invention may be used with a wide variety of sequencing modalities and are suitable for sequencing single molecules. Additionally, the optical detection devices consistent with the present invention have simplified design, assembly, and production relative to existing biochip devices. For example, the nucleic acids to be sequenced can be affixed to random linker sites on the array, avoiding the use of time consuming and expensive robotics to deposit or synthesize nucleic acids at predetermined locations.

The bioassay system consistent with the present invention can be used as part of a system in methods and processes for biomolecule detection, including nucleic acid hybridization or sequencing for, e.g., whole genome sequencing, transcriptional profiling, comparative transcriptional profiling, or gene identification. Biomolecule detection can also include detection and/or measurement of binding interactions, e.g., protein/protein, antibody/antigen, receptor/ligand, and nucleic acid/protein. These applications are useful for analytical or diagnostic processes and methods.

Nucleic acids suitable for detection on the system provided by the invention may, in some embodiments, be part of a linking molecule, which affixes a molecule suitable for assaying binding interactions, e.g., proteins, other nucleic acids, carbohydrate moieties, or small molecules to a linker site on a device provided by the invention. The linking molecule may, in some embodiments, further comprise a capture molecule, which binds to the molecule being assayed for binding interactions. The nucleic acid in a linking molecule serves as an identifying tag for the capture molecule of the linking molecule by, e.g., direct sequencing or hybridization.

The methods provided by the invention typically comprise a step of affixing a molecule to be detected to an address array of a device provided by the invention. In some embodiments, the address array may include a blind sheet 230 having a plurality of pinholes 235, and linker sites 220 may be formed in or around pinholes 235. See, for example, FIGS. 1 and 2. Thus, the bioassay system consistent with the present invention can simultaneously read millions of nucleic acid segments. If each segment is, for example, 1000 bases long, a single device could obtain billions of bits of sequence information, making, e.g., whole genome sequencing and resequencing possible.

2.1 Molecules to be Detected

Nucleic acids suitable for detection by the methods provided by the invention can include any nucleic acid, including, for example, DNA, RNA, or PNA (peptide nucleic acid), and can contain any sequence—both known and unknown, including naturally occurring or artificial sequences. The nucleic acid may be naturally derived, recombinantly produced, or chemically synthesized. The nucleic acid may comprise naturally-occurring nucleotides, nucleotide analogs not existing in nature, or modified nucleotides. The length of the nucleic acid to be detected will vary based on the actual application. In some embodiments, the nucleic acid includes at least 10, 20, 50, 100, 200, 500, 1000, 2000, 5000, 10000, 20000 bases, or more. In some embodiments, the nucleic acid may be from 10 to 20, from 10 to 50, from 10 to 100, from 50 to 100, from 50 to 500, from 50 to 1000, from 50 to 5000, from 500 to 2000, from 500 to 5000, or from 1000 to 5000 bases.

A nucleic acid can be single-stranded for detection. Single stranded nucleic acid templates can be derived from a double stranded molecule by means known in the art including, for example, heating or alkali or other chemical treatment. Single stranded nucleic acid templates can also be produced by, e.g., chemical or in vitro synthesis.

In some embodiments, the nucleic acid to be detected is attached to a linker site at its 5' or 3' end. In some embodiments, the nucleic acid may further comprise one or more end link primers coupled to the 5' end, the 3' end, or both the 5' end and the 3' end of the nucleic acid. In particular embodiments, an end link primer is affixed to the 3' end of the nucleic acid. End link primers can be used both to affix the nucleic acid to be detected to linker sites on the device and provide a complementary sequence for one or more detecting primers, e.g., a sequencing primer.

2.1.1 End Link Primer

End link primers are short nucleic acid molecules usually composed of less than 100 nucleotides. In some embodiments, the end link primer is at least 5, 10, 15, 20, 25, 30, 50, 75, 90 nucleotides, or more, in length. In certain embodiments, end link primers are from 8 to 25, from 10 to 20, from 10 to 30, or from 10 to 50 nucleotides in length. In some embodiments, the end link primers are unbranched, however, in other embodiments, they may be branched.

The end link primer can be used to attach the nucleic acid to be detected to a linker site on the address array. In some embodiments, the end link primer may link the nucleic acid to the array surface directly, e.g., by covalent linkage (e.g., ester or thiol linkage) or non-covalent linkage, e.g., antigen/antibody or biotin/avidin binding. See, e.g., FIG. 5, FIG. 6, and FIG. 7. In some embodiments, the end link primer may link the nucleic acid to the array surface indirectly, e.g., by binding an intermediate molecule, e.g., a polymerase. See, e.g., FIG. 8. Accordingly, the end link primer can contain modified nucleotides or be otherwise modified to facilitate attachment to a linker site by means known in the art, e.g., disulfide, thioester, amide, phosphodiester, or ester linkages; or by, e.g., antibody/antigen or biotin/avidin binding, e.g., the end link primer contains a nucleotide comprising an antigen moiety or a biotinylated nucleotide. In particular embodiments, a modified nucleotide is on the 3' end of an end link primer. In some embodiments, the 5' end of an end link primer contains a modified nucleotide.

The end link primer can also serve as a complement to one or more primers used to detect the nucleic acid, e.g., a sequencing primer. In some embodiments, the primer is used to detect the nucleic acid by hybridization, e.g., the primer contains a detectable label, e.g., a fluorescent or radioisotopic label. In some embodiments, the 5' end of the end link primer comprises a sequence complementary to a sequencing primer. In some embodiments, the end link primer sequence that is complementary to the sequencing primer is oriented so that the 3' end of the sequencing primer is immediately adjacent to the first nucleotide in the nucleic acid to be sequenced.

Figure 6:
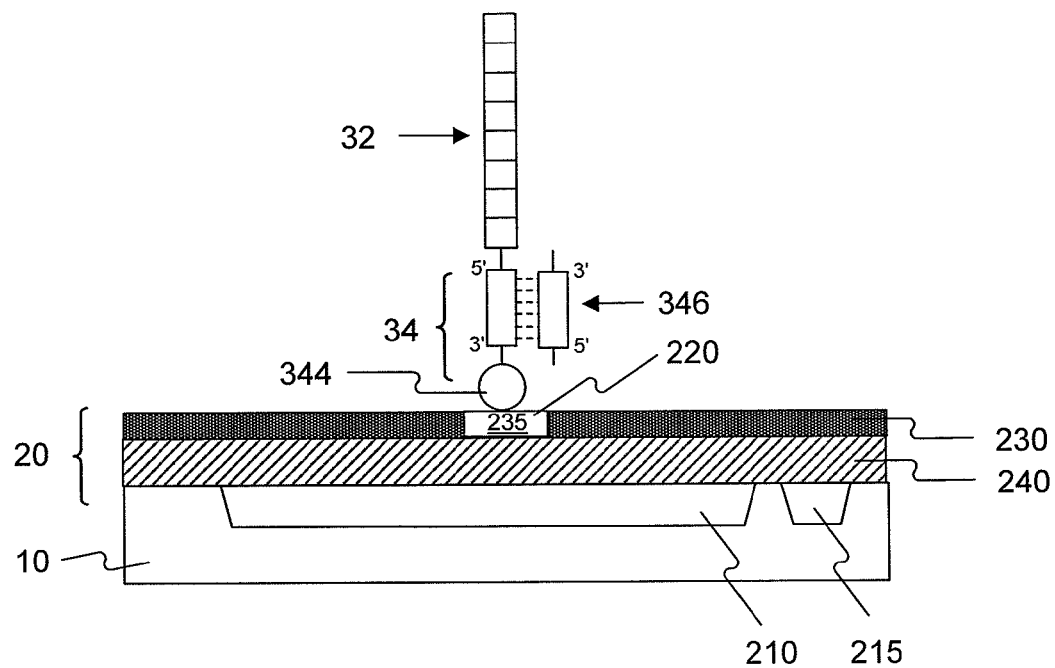
FIG. 6 illustrates a nucleic acid linked on a linker site of a device consistent with the present invention.

For example, FIG. 6 is a graphical representation of one embodiment of a nucleic acid to be sequenced affixed to a optical detection apparatus 20 consistent with the present invention. A single-stranded nucleic acid 32, end link primer 34, and annealed sequencing primer 346 are affixed at a linker site 220 treated to have reactive functional groups, which bind a modified nucleotide 344 on end link primer 34. In some embodiments, nucleic acid 32 may be attached to linker site 220 via its 5' end, and end link primer 34 may be attached to the 3' end of nucleic acid 32 to serve as a complement to sequencing primer 346.

In some embodiments, end link primers are added to ends of the nucleic acid to be detected by a ligase, for example, a DNA ligase. In some embodiments, the end link primer and nucleic acid to be detected are both single stranded before the ligation. In other embodiments, both are double stranded. In still other embodiments, one is single stranded and the other is double stranded. Ligation is well known in the art. For example, in the polony sequencing method, Shendure et al. (*Science*, 309:1728-1732 (2005)) ligated a T30 end link primer (32 bp) to a sample DNA segment with the New England Biolabs' (NEB) Quick Ligation kit. There, the ligation reaction solution included 0.26 pMole of DNA, 0.8 pMole of T30 end link primer, 4.0 µl T4 DNA Ligase, in 1× Quick Ligation Buffer. After mixing, the reaction solution was incubated for about 10 minutes at room temperature, and then placed on ice. The ligation reaction was stopped by heating the samples to 65° C. for 10 minutes.

In other embodiments, the end link primer may be synthesized on the nucleic acid to be detected. For example, the end link primer may be a homopolymer added by, e.g., terminal transferase. For example, Harris et al., (*Science* 320:106-109 (2008)) added a poly A tail to DNA templates, which served as the complement to a poly T sequencing primer in the single molecule sequencing of a viral genome.

2.1.2 Sequencing Primer

A sequencing primer is a single-stranded oligonucleotide complementary to a segment of the nucleic acid to be detected or its associated end link primer. In some embodiments, the sequencing primer is at least 8, 10, 15, 20, 25, 30, 35, 40, 45, 50 nucleotides, or more in length. In particular embodiments, the sequencing primer may be from 8 to 25, from 10 to 20, from 10 to 30, or from 10 to 50 nucleotides in length. The sequencing primer can be made up of any type of nucleotide, including naturally-occurring nucleotides, nucleotide analogs not existing in nature, or modified nucleotides. In certain embodiments, the 5'-end of a sequencing primer may be modified to facilitate binding to a linker site on the address array after the sequencing primer hybridizes with a nucleic acid to be sequenced, including one or more end link molecules.

In some embodiments, a sequencing primer contains modified nucleotides, e.g., locked nucleic acids (LNAs; modified ribonucleotides, which provide enhanced base stacking interactions in a polynucleic acid). As an illustration of the utility of LNAs, Levin et al. (Nucleic Acid Research 34(20):142 (2006)) showed that a LNA-containing primer had improved specificity and exhibited stronger binding relative to the corresponding unlocked primer. Three variants of the MCP1 primer (5'-cttaaattttcttgaat-3') containing 3 LNA nucleotides (in caps) at different positions in the primer were made: MCP1-LNA-3'(5'-cttaaatfttCtTgaAt-3'); MCP1-LNA-5'(5'-CtTaAattttcttgaat-3'); and MCP1-LNA-even (5'-ctTaaatTttct-Tgaat-3'). All LNA-substituted primers had enhanced Tm, while the MCP1-LNA-5' primer exhibited particularly enhanced sequencing accuracy (Phred Q30 counts). Accordingly, in particular embodiments, the sequencing primer may contain at least one locked nucleotide in its 5' region, i.e., the 5' half, third, or quarter of the sequencing primer.

Sequencing primers and single stranded sample nucleic acids (i.e., a nucleic acid to be detected including at least one end link primer) may be hybridized before being applied to an optical detection device consistent with the present invention. The sequencing primer and sample nucleic acid may be hybridized by mixing the sample nucleic acid with a molar excess of sequencing primer in a salt-containing solution, such as 5×SSC (or 5×SSPE), 0.1% Tween 20 (or 0.1% SDS), and 0.1% BSA buffer. The mixture may be heated to 65° C. for at least 5 minutes and slowly cooled to room temperature, to allow primer/template annealing. Residual primers can be eliminated by appropriate means including, e.g., a molecular sieve.

Primers, including both end link and sequencing primers, can be designed by appropriate means, including visual inspection of the sequence or computer-assisted primer design. Numerous software packages are available to assist in the primer design, including DNAStar™ (DNAStar, Inc., Madison, Wis.), OLIGO 4.0 (National Biosciences, Inc.), Vector NTI® (Invitrogen), Primer Premier 5 (Premierbiosoft), and Primer3 (Whitehead Institute for Biomedical Research, Cambridge, Mass.). Primers are designed taking into account, for example, the molecule to be sequenced, specificity, length, desired melting temperature, secondary structure, primer dimers, GC content, pH and ionic strength of the buffer solution, and the enzyme used (i.e., polymerase or ligase). See, e.g., Joseph Sambrook and David Russell, Molecular Cloning: A Laboratory Manual Cold Spring Harbor Laboratory Press; 3rd edition (2001).

2.1.3 Bonding to the Array Surface

After the sequencing primer and nucleic acid to be sequenced, including one or more end link primers, are annealed, this complex is prepared in a suitable buffer, applied to the surface of an address array, and allowed to bind. In some embodiments the sample nucleic acid (nucleic acid to be detected and one or more end link primers) are affixed to linker sites and sequencing or detecting primers are later applied. In other embodiments, the complex is hybridized before being applied to a device. Linker sites where only one sample nucleic acid is bound are known as effective addresses. In certain embodiments, the complex is applied to the optical detection device and the sample nucleic acids affix to random linker sites on the address array. In other embodiments, sample nucleic acids can be applied to predetermined linker sites on the address array by appropriate means, including, e.g., by robotics or liquid handling systems.

Appropriate means for affixing nucleic acids to a solid support are well known in the art. In some embodiments, the sample nucleic acid may be affixed directly to a linker site by covalent linkage, e.g., disulfide, thioester, amide, phosphodiester, or ester linkages; or by non-covalent linkage, e.g, antibody/antigen or biotin/avidin binding. In some embodiments, the sample nucleic acid may be affixed to a linker site by an intervening molecule. In some embodiments, the intervening molecule may be a polymerase, e.g., a DNA polymerase.

As an illustrative example of direct, covalent attachment of a nucleic acid, Adeesi et al. (Nucleic Acid Research, 28:87 (2000)) modified the 5' end of a primer to include a SH functional group. According to the method of Adeesi et al., a nucleic acid may be prepared in 50 μM phosphate buffered saline ("PBS") (NaPi: 0.1 MNaH$_2$PO$_4$ pH 6.5, 0.1 M NaCl). About 1-5 μl of primer solution may then be applied to a surface of a silanised glass slide and incubated in a humidity control box at room temperature for about 5 hours to bond the primer to the chip surface. After the binding reaction is completed, the PBS solution is vibration washed twice at room temperature for 5 minutes each to remove un-bonded DNA. After cleaning, 10 mM β-mercaptoethanol is added to a PBS solution and used to rinse the address array surface under room temperature, to deactivate the thiol group of un-bonded DNA. Next, the array surface is washed, e.g., once with 5×SSC 0.1% Tween and once with 5×SSC buffer solution. Accordingly, in some embodiments, the method used by Adeesi et al. can be used in the methods provided by the invention to affix the sample nucleic acid complex to a linker site, e.g., via the 5' end of a sequencing primer or the sample nucleic acid.

In an alternative embodiment, the sample nucleic acid may comprise, e.g., a biotinylated nucleotide, and binds to avidin on the linker site surface. In another embodiment, the sample nucleic acid may comprise an antigenic moiety, e.g., BrdU or digoxigenin, that is bound by an antibody (or fragment thereof) on the linker site. By "antibody" it is to be understood that this term includes fragments of immunoglobin molecules, including, for example, one or more CDR domains; or variable heavy or variable light fragments. Antibodies may be naturally occurring, recombinant, or synthetic. Antibodies may also include, e.g., polyclonal and monoclonal variants. In some embodiments the antibodies bind their antigen(s) with association constants of at least $10^6$, $10^7$, $10^8$, $10^9$ M, or higher. The structure, function, and production of antibodies are well known in the art. See, for example, Gary Howard and Matthew Kasser, *Making and Using Antibodies: A Practical Handbook* CRC Press; 1$^{st}$ edition (2006).

Figure 8:
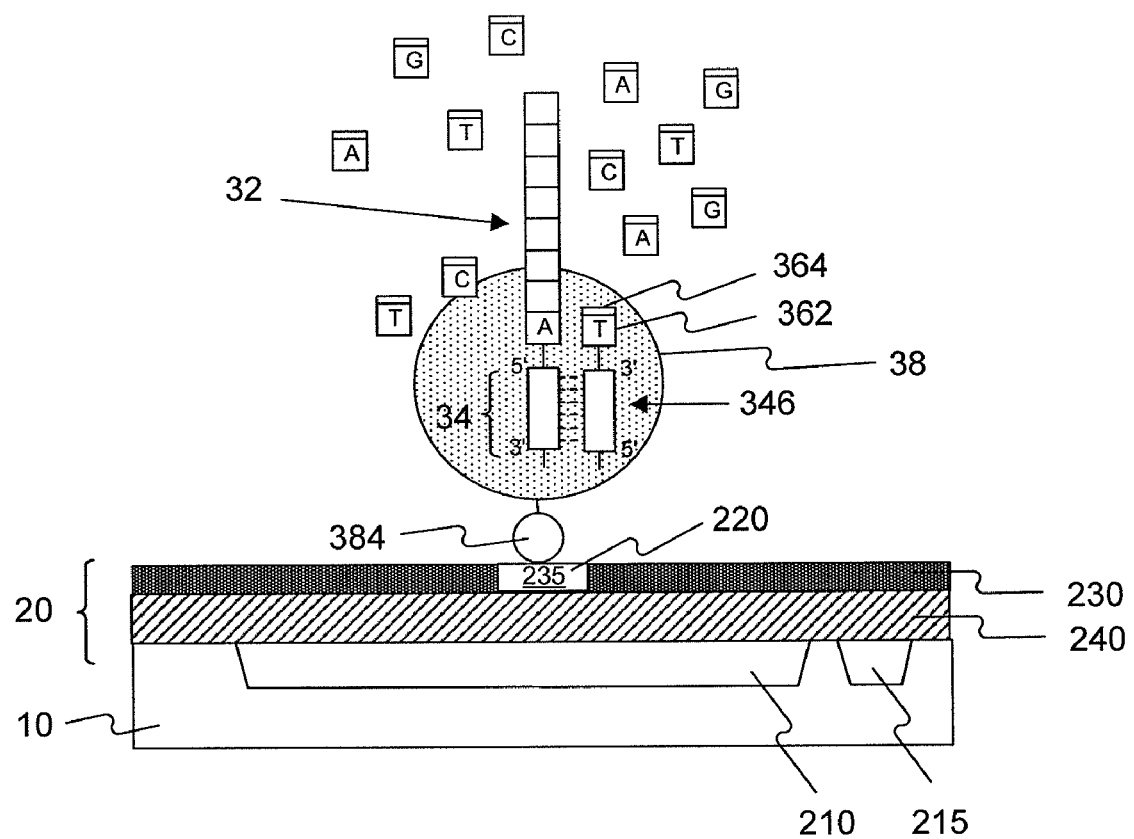
FIG. 8 illustrates an alternative embodiment of the base extension sequencing reaction shown in FIG. 7.

In yet another embodiment, the sample nucleic acid may be affixed to the linker site by a polymerase, e.g., DNA polymerase. The skilled artisan will appreciate, that to retain enzyme function available information, such as the primary, secondary, and tertiary structures of the enzyme, should be taken into consideration. For example, the structures of Taq and Phi29 polymerases are known in the art, see: Kim et al., *Nature*, 376:612-616 (1995) and Kamtekar et al., *Mol. Cell,* 16:609-618 (2004), respectively. Means for fixing a polymerase to a surface, while retaining activity are known in the art and are described in, e.g., U.S. Patent Application Publication No. 2008/0199932, published Aug. 21, 2008 and Korlach et al. *PNAS* 105:1176-1181 (2008). FIG. 8 is a graphical representation of one embodiment of the invention where the sample nucleic acid (i.e., nucleic acid to be sequenced 32, end link primer 34, and sequencing primer 346) is bound to a linker site 220 via a polymerase 38 already bound at linker site 220 by means 384, e.g., direct non-covalent adsorption, an antibody, biotin, or chemical linkage, e.g., amide bond.

In some embodiments, an aldehyde-modified surface of a linker site is treated with aldehyde-containing silane reagent. The aldehydes readily react with primary amines on the proteins to form a Schiff's base linkage. Because many proteins display lysines on their surfaces in addition to the generally more reactive α-amine at the NH$_2$-terminus, they can attach to the slide in a variety of orientations, permitting different sides of the protein to interact with other proteins or small molecules in solution. In another embodiment, a photoNHS (a N-hydroxy succimido carboxylate molecule linked to a azidonitrobenzene molecule with a carbon chain linker) attaches to an amine-modified surface on the device by UV photoactivation. In these embodiments, UV light excites the azidonitrobenzene moiety to produce highly reactive nitrene, by eliminating nitrogen. Nitrene is readily reacts with NH$_2$ on the surface of the device and form a hydrazine bond. The other end of the linker is NHS carboxylate, which react with lysines on the surface of polymerase to produce an amide covalent bond. In another embodiment, an NHS carboxylate moiety is reacted with primary amine on the surface of the device under buffered conditions. UV light is used to activate an azidonitrobenzene moiety and form a highly reactive nitrene as an electron deficient group and readily react with primary amine of lysine residues on the polymerase. These methods are described in further detail in Example 4, below.

2.2 Sequencing Modalities

The bioassay system provided by the present invention can be used to detect and sequence nucleic acids by means known in the art, as reviewed in, e.g., U.S. Pat. No. 6,946,249 and Shendure et al., *Nat. Rev. Genet.* 5:335-44 (2004). In some embodiments, the sequencing methods rely on the specificity of either a DNA polymerase or DNA ligase and include, e.g., base extension sequencing (single base stepwise extensions), multi-base sequencing by synthesis (including, e.g., sequencing with terminally-labeled nucleotides) and wobble sequencing, which is ligation-based. All of the methods typically require a single stranded sample nucleic acid, including at least one end link primer to be affixed at a linker site (either directly or indirectly). Sequencing is then initiated at a sequencing primer (ligase-based sequencing commonly refers to anchor primers, which serve the analogous purpose to sequencing primers).

For all sequencing modalities, the present invention offers the advantage of being able to resequence single molecules. For example, after completion of a sequencing read, the sequencing primer and extended nucleotides can be stripped from the sample nucleic acid, the device is washed, and the sequencing is repeated. In various embodiments, the resequencing may be done by the same or different methods. By resequencing the same molecule, sequencing errors are expected to fall as the power of the number of sequencing reads. For example, if per base error rates for a single read are $10^{-3}$, then after two reads, this falls to $(10^{-3})^2$, i.e., $10^{-6}$. This is particularly advantageous for single molecule sequencing since the modified nucleotides used for sequencing can lose their labels or blocking groups resulting in, e.g., spurious deletions.

2.2.1 Base Extension Sequencing: Stepwise Extension

In some embodiments, the light detection apparatuses provided by the invention can be used to perform base extension sequencing as disclosed in, e.g., U.S. Pat. No. 5,302,509. In some embodiments, base extension sequencing begins by attaching a partial duplex sample nucleic acid comprising a single stranded nucleic acid to be sequenced 32, an end link primer 34 associated with the 3' end of nucleic acid to be sequenced 32, and a sequencing primer 346 annealed thereto, to a linker site 220, as depicted in FIG. 6. In some embodiments, polymerase 38 and modified nucleotides are then applied to the light detection apparatus in a suitable buffer. In some embodiments, the sample nucleic acid complex is affixed to the linker site by a polymerase at a linker site. In some embodiments, the nucleotides include a covalently-linked detectable label, e.g., a fluorescent label, and a blocking group to prevent any secondary extension. Accordingly, the sequencing pauses after the addition of a single nucleotide to the 3' end of sequencing primer 346.

Figure 7:
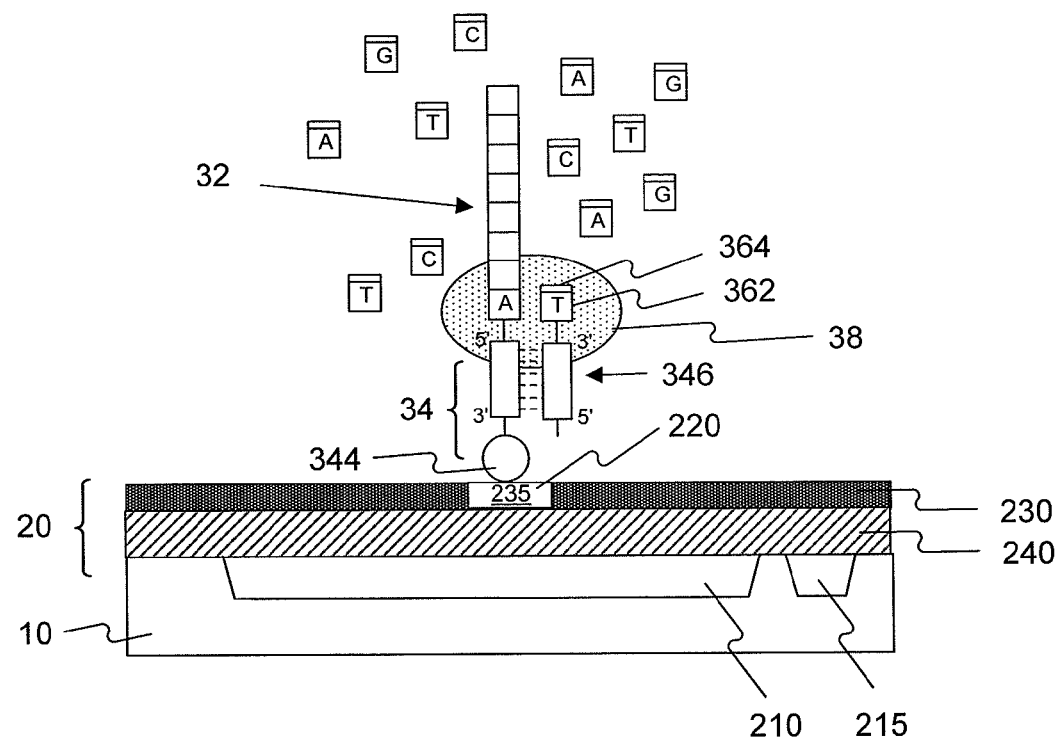
FIG. 7 illustrates a nucleic acid linked on a linker site of the device after one round of base extension with blocked and labeled nucleotides.
Figure 9:
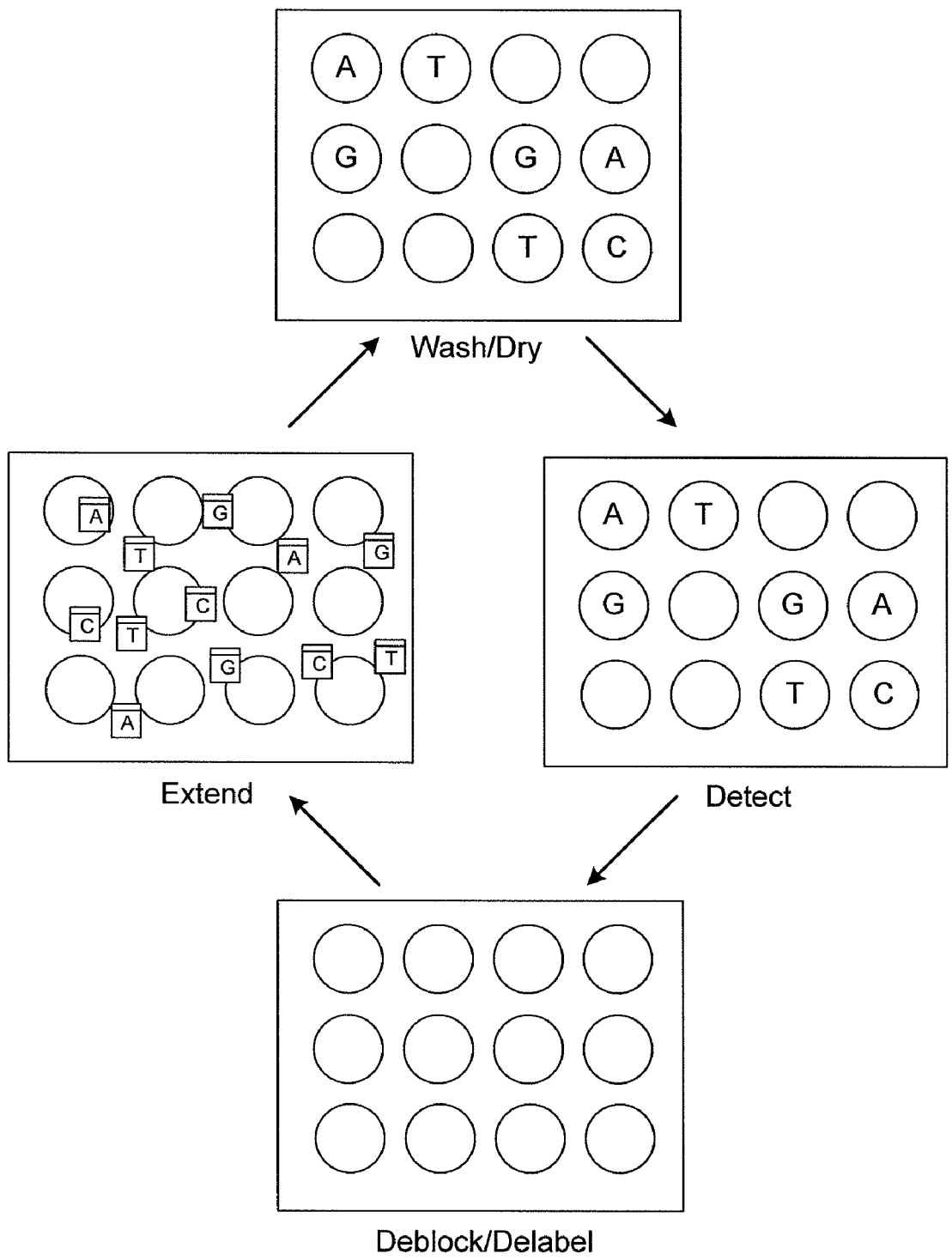
FIG. 9 illustrates one round of sequencing several nucleic acids in parallel by base-extension sequencing.

FIG. 7 is a graphical representation of the first step of one embodiment of a base extension sequencing reaction. A nucleotide 362 with a fluorescent blocking group 364 is added by a DNA polymerase 38 to the 3' end of sequencing primer 346. In some embodiments, the fluorescent label acts as the blocking group. In other embodiments, they are separate moieties. A single nucleotide is incorporated at the 3' end of sequencing primer 346 and is identified by its label by the corresponding light detector 210. The fluorescent label and blocking group are then removed, e.g., by chemical or enzymatic lysis, to permit additional cycles of base extension. In certain embodiments, the label and blocking groups can be removed simultaneously or sequentially and in any order. By compiling the order of the bases added, the sequence of the sample nucleic acid is deduced in the 3' to 5' direction, one base at a time. FIG. 9 illustrates one cycle of extension, detection, and deblocking/delabeling of several sample nucleic acids in parallel.

Generally, there are two ways to recognize the nucleotide added during stepwise extension. In the first case, the four nucleotides all have the same detectable label, but are added one at a time, in a predetermined order. The identity of the extended nucleotide is determined by the order that the nucleotide is added in the extension reaction. In the second mode for recognizing the base integrated during extension, four different nucleotides are added at the same time and each is coupled with a distinct detectable label. In different embodiments, the excitation or emission spectra and/or intensity of the labels may differ. The identity of the nucleotide added in the extension is determined by the intensity and/or wavelength (i.e., excitation or emission spectra) of the detected label. Examples of these two methodologies are presented in Example 5.

2.2.2 Sequencing By Synthesis: Multi-step Extension

In some embodiments, sequencing by synthesis may proceed with multiple uninterrupted extensions, e.g., without the use of blocking groups. In these embodiments, the polymerization reaction in monitored by detecting the release of the pyrophosphate after nucleoside triphosphate hydrolysis, i.e., the release of the β and γ phosphate complex. This complex can be detected directly, for example, by a fluorescent moiety on the complex, or indirectly, by coupling the pyrophosphate to a chemi- or bio-luminescent detection system.

In some embodiments, the sample nucleic acid is sequenced essentially continuously by using terminal-phosphate-labeled nucleotides. Exemplary embodiments of terminal-phosphate-labeled nucleotides and methods of their use are described in, e.g., U.S. Pat. No. 7,361,466 and U.S. Patent Publication No. 2007/0141598, published Jun. 21, 2007. Briefly, the nucleotides are applied to the apparatuses provided by the invention and, when hydrolyzed during the polymerization, the labeled pyrophosphate is detected by a corresponding light detector. In some embodiments, all four nucleotides comprise distinct labels and can be added simultaneously. In some embodiments, the nucleotides comprise indistinguishable, e.g., identical, labels and are added sequentially in a predetermined order. Sequential, cyclical addition of nucleotides with indistinguishable labels still permits multiple, uninterrupted polymerization steps, e.g., in homopolymer sequences.

2.2.3 Ligase-Based Sequencing

In other embodiments, a sample nucleic acid is sequenced on the optical detection apparatuses provided by the invention by ligase-based sequencing. Ligase-based sequencing methods are disclosed in, for example, U.S. Pat. No. 5,750,341, PCT publication WO 06/073504, and Shendure et al. Science, 309:1728-1732 (2005). In the method of Shendure et al., for example, an unknown single-stranded DNA sample may be flanked by two end link primers and immobilized on a solid support. A particular position in the unknown sequence (e.g., the $n^{th}$ base proximal to a particular end link primer) can be interrogated by annealing a so-called anchor primer (which is analogous to a sequencing primer) to one of the end link primers and then applying a pool of 4 degenerate nonamers to the mixture. The four nonamers all have distinct fluorescent labels and are degenerate at all positions except for the query position, where each nonamer interrogates with a distinct base—A, C, G, or T. The sample is washed, fluorescently scanned, and the query base is identified. The anchor primer and ligated nonamer are then stripped from the sample nucleic acid, the device is washed, and the process is repeated, querying a different position. Advantageously, this method is non-progressive, i.e., bases need not be queried in order. Thus, errors are not cumulative. Additionally, this method can query nucleotides from either the 5' or 3' direction, i.e., does not require canonical 5'→3' DNA synthesis. A total of about 13 bases of a sample nucleic acid can typically be sequenced by this method.

2.3 Applications

The bioassay system consistent with the present invention can simultaneously detect millions of nucleic acid segments. If each segment is, for example, 1000 bases long, a single device could obtain upwards of billions of base sequences at once. Discussed below are additional applications of the devices and methods provided herein.

2.3.1 Whole Genome Sequencing

The bioassay system consistent with the present invention can be used to perform whole or partial genome sequencing of, e.g., a virus, bacterium, fungi, eukaryote, or vertebrate, e.g., a mammal, e.g., a human.

Genomic DNA can be sheared into fragments of at least 20, 50, 100, 200, 300, 500, 800, 1200, 1500 nucleotides, or longer, for sequencing. In some embodiments, the sheared genomic DNA may be from 20 to 50, from 20 to 100, from 20 to 500, from 20 to 1000, from 500 to 1200, or from 500 to 1500 nucleotides long. In some embodiments, the nucleic acids to be sequenced, along with associated end link primers, are made single stranded, annealed to a sequencing primer, and applied to a device provided by the invention for sequencing as described above.

2.3.2 Gene Expression Profiling

In other embodiments, the bioassay system consistent with the present invention can be used to sequence cDNA for gene expression profiling. For example, mRNA levels can be quantified by measuring the relative frequency that a particular sequence is detected on a device. Several million cDNA molecules can sequenced in parallel on a device provided by the invention. If a cell contains, on average, 350,000 mRNA molecules, a transcript present at even one copy per cell is expected to be sequenced approximately three times in one million sequencing reactions. Accordingly, the devices provided by the invention are suitable for single molecule sequencing with single copy number sensitivity.

cDNA synthesis is well known in the art and typically includes total RNA extraction with optional enrichment of mRNA. cDNA is produced from mRNA by steps including, for example: reverse transcription, for first strand synthesis; RNAse treatment, to remove residual RNA; random hexamer priming of the first strand, and second strand synthesis by DNA polymerase. The resultant cDNA is suitable for sequencing on the devices provided by the invention. Methods of isolating and preparing both DNA and RNA are well known in the art. See, for example, Joseph Sambrook and David Russell, *Molecular Cloning: A Laboratory Manual* Cold Spring Harbor Laboratory Press; 3rd edition (2001).

In some embodiments, cDNA can be sequenced by methods as disclosed in U.S. Pat. Nos. 6,812,005 and 7,361,488. Briefly, cDNA is ligated with adapter poly nucleic acids, the adapters are processed with specialized restriction enzymes, and finally, the processed nucleic acids bind to complementary oligonucleotides affixed at linker sites of a device provided by the invention. In particular embodiments, the adapter molecules are end link primers.

In some embodiments consistent with the present invention, the poly-A tail of an mRNA can serve as a suitable end link primer, which is complementary to a poly T sequencing primer.

2.3.3 Detecting and/or Measuring Binding Interactions

In other embodiments, the bioassay system can be used to detect various binding interactions including, e.g., DNA/DNA, RNA/RNA, or DNA/RNA base pairings, nucleic acid/protein interactions, antigen/antibody, receptor/ligand binding, and enzyme/substrate binding. In general, a sample molecule is affixed to a linking molecule that comprises an identifying nucleic acid tag (ID). In some embodiments, the linking molecule further comprises a capture molecule that binds the sample molecule. The linking molecule also comprises a means for binding to a linker site; e.g., a moiety to facilitate covalent chemical linkage, such as disulfide, thioester, amide, phosphodiester, or ester linkages; or by non-covalent linkage, e.g., antibody/antigen or biotin/avidin binding. In some embodiments, a linking molecule is affixed to the array by the ID tag.

A sample molecule is applied to a device consistent with the present invention and affixed to a random linker site by its linker molecule, e.g., by binding a capture molecule located on the linking molecule. In some embodiments, the sample molecule and linker molecules are mixed, allowed to bind, and then applied to a device provided by the invention. In some embodiments, the linker molecule is first applied to the device, allowed to affix to a linker site, and then the sample molecule is applied. Next, the ID is detected (e.g., by hybridization or sequencing) by the methods consistent with the invention to identify the associated sample molecule. A plurality of sample molecule species can be affixed to the same array and are distinguished by their label while their binding interactions can be characterized using the unique IDs of the capture molecule it binds to. Thus, in some embodiments, a method of detecting a labeled sample molecule comprises the steps of linking a sample molecule to a linker site of a device consistent with the present invention by a linker molecule comprising a nucleic acid tag (ID), performing nucleic acid sequencing of the ID, and detecting the labeled sample molecule. In particular embodiments, the nucleic acid sequencing is base extension sequencing. In some embodiments the nucleic acid sequencing is chosen from ligase-based sequencing, or terminal-phosphate-labeled nucleotide sequencing.

By using nucleotide "bits," up to $4^n$ distinct capture molecules can be affixed and identified on the bioassay system consistent with the present invention, where n is natural number representing the length of the ID sequenced. For example, 5 nucleotides could provide over a thousand unique IDs, while 12 nucleotides provide over 16 million combinations. For example, linker molecules are affixed to a device consistent with the present invention and their locations are determined by detecting their corresponding ID tag. The linker molecules then serve as probes to, e.g., investigate binding interactions with one or more labeled sample molecules. That is, a device with one or more linker molecules affixed to it can serve as a probe array.

In certain embodiments, the labeled sample molecules are fluorescently labeled. When bound to the capture molecule of a linker molecule, a labeled sample molecule is detected by the light detector(s) corresponding to the linker site where the linker molecule is affixed. Accordingly, in some embodiments, methods consistent with the present invention may further comprise the steps of applying a labeled sample molecule to a device consistent with the present invention and detecting the labeled sample molecule. In particular embodiments, the device has linker molecules comprising a nucleic acid tag (ID) affixed to its linker sites. Multiple labeled sample molecules can be applied to a probe array simultaneously and be differentiated by their labels, e.g., by the intensity and/or wavelength of their fluorescent labels. Dissociation constants for binding interactions between sample molecules and labeled query molecules can be inferred based on both kinetics (e.g., rates of docking/undocking) and statistics (e.g., the portions of sample molecules in the bound or unbound state at any given time) at a given concentration of a labeled query molecule.

In some embodiments, the ID of a linking molecule is at least 5, 10, 15, 20, 25, 30, 40, 50, 75, 90, 100, 150, 200, or more, nucleotides long. In some embodiments, the ID is from 5 to 10, 20, 40, 80, or 160; or from 10 to 20 or 50; or from 20 to 35 nucleotides long. The ID contains a unique nucleic acid sequence, i.e., a nucleic acid to be detected. In particular embodiments, the unique nucleic acid sequence can be at least 1, 2, 4, 6, 8, 10, 12, 14, 16, 20, 24, 30, or more nucleotides long. In some embodiments, the unique nucleic acid sequence is from 4 to 10, 12, 15, or 20; or from 10 to 20 nucleotides long. The ID comprises at least one end link primer, i.e., the ID contains a sequence complementary to a sequencing primer, which, in some embodiments, is modified to attach to a linker site, e.g., by containing a biotinylated nucleotide. In some embodiments, the end link primer portion of the ID is 3' to the unique nucleic acid sequence. In some embodiments, it is 5' to the unique nucleic acid sequence. In still other embodiments, end link primers are present at both the 3' and 5' ends of the unique nucleic acid sequence.

In certain embodiments, sample molecules and capture molecules comprise moieties chosen from a carbohydrate, lipid, protein, peptide, antigen, nucleic acid, hormone, small organic molecule (e.g., a pharmaceutical), or vitamin moiety;

or a combination thereof. These moieties may be naturally-occurring (e.g., biochemically purified) or synthetic (e.g., chemically synthesized or recombinantly produced). Additionally, these substrates may contain no, some, or all non-native components (e.g. non-natural amino acids, blocking or protecting groups, etc.). In particular embodiments, a sample molecule or capture molecules are proteins, e.g., a growth factor, peptide antigen, antibody, or receptor.

Various means for conjugating nucleic acids to linker molecules or linker sites are known in the art, as reviewed in, e.g., U.S. Patent Publication No. 2004/0038331. The '331 publication discloses methods of forming protein oligonucleotide conjugates on a solid-phase support. U.S. Pat. No. 4,748,111 provides one example of conjugating a protein to the 3' end of a nucleic acid. There, terminal transferase is first used to add a ribose residue to the 3' portion of the molecule. A periodate oxidation reaction then generates a 3' aldehyde group on the nucleic acid, which then forms a covalent bond with an amide group of a protein. When a protein is conjugated to the 3' end of the ID, attachment to a linker site is via the 5' end of the ID.

In some embodiments, a capture molecule, e.g., a protein, is linked to the 5' end of an ID. In these embodiments, the 3' end of the ID or 5' end of a sequencing primer is used to affix capture molecule to a linker site. U.S. Pat. No. 6,013,434, for example, discloses oligonucleotide-polyamide conjugates, where the connection is via the 5' end of the oligonucleotide. U.S. Pat. No. 6,197,513 discloses both PNA and DNA conjugates to molecules with carboxylic acid moieties, e.g., proteins, via the 5' end of the nucleic acid. The PNA and DNA molecules contain arylamine or aminooxyacetyl moieties. U.S. Pat. No. 6,153,737 discloses oligonucleotides containing at least one 2' functionalized nucleoside, suitable for conjugating a variety of molecules to it.

2.3.4 Additional Detection Methods

2.3.4.1 FRET

In some embodiments, a molecule is detected on a light detection apparatus provided by the invention by Förster resonance energy transfer (FRET), sometimes known as fluorescence resonance energy transfer. As is known in the art, FRET occurs when an excited donor molecule non-radiatively transfers energy to an acceptor molecule, which emits the energy, typically as light. FRET can help reduce background signals by, e.g., providing greater spectral separation between effective excitation and emission wavelengths for a molecule being detected. FRET is often used to detect close molecular interactions since its efficiency decays as the sixth power of the distance between donor and acceptor molecules. For example, Zhang et al. (*Nature Materials* 4:826-31 (2005)) detected nucleic acid hybridization by FRET. There, a biotinylated nucleic acid target was conjugated to an avidin-coated quantum dot donor, which then excited a Cy5-conjugated DNA probe. In some embodiments of the invention, a labeled capture molecule and labeled sample molecule may form a donor/acceptor (or vice versa) pair for detection by FRET.

In some embodiments of nucleic acid sequencing provided by the invention, fluorescently labeled nucleotides act as acceptor chromophores for a donor chromophore attached to a polymerase or ligase. Accordingly, in these embodiments, the donor chromophore located on the polymerase or ligase excites an acceptor chromophore on a nucleotide being polymerized on, or ligated to, the sample nucleic acid. Nucleotides not proximate to the polymerase are not excited due to the rapid falloff in FRET efficiency. In some embodiments the donor molecule is, e.g., another fluorophore, e.g., a quantum dot. Quantum dots, e.g., semiconductor quantum dots are known in the art and are described in, e.g., International Publication No. WO 03/003015. Means of coupling quantum dots to, e.g., biomolecules are known in the art, as reviewed in, e.g., Mednitz et al., *Nature Materials* 4:235-46 (2005) and U.S. Patent Publication Nos. 2006/0068506 and 2008/0087843, published Mar. 30, 2006 and Apr. 17, 2008, respectively. In some embodiments, quantum dots are conjugated to a DNA polymerase molecule, which is described further in Example 3, below. As already discussed above for conjugating enzymes to linker sites, the skilled artisan will undoubtedly appreciate that when conjugating fluorophores to, e.g., a DNA polymerase or ligase, care must be taken to retain enzyme function by mitigating any effect of conjugating the fluorophore on the primary, secondary, and tertiary structures of the enzyme.

2.3.4.2 Multi Photon Excitation

In some embodiments, a chromophore is excited by two or more photons. For example, in some embodiments, excitation of either a donor or acceptor chromophore in FRET is via two or more photons. Two photon and multi-photon excitation are described further in, e.g., U.S. Pat. Nos. 6,344,653 and 5,034,613.

2.3.4.3 Time Resolved Detection

In some embodiments, the light source and light detectors of a device provided by the invention can be modulated to have a characteristic phase shift. Using methods known in the art, for example, as disclosed in U.S. Patent Publication No. 2008/0037008, published Feb. 14, 2008, light emitted from a molecule being detected on a device provided by the invention can be measured by a corresponding light detector without interference from an excitation light source.

3. Biomolecule Analysis Service Using the Bioassay System

The present invention also provides a method of providing biomolecule analysis service using the bioassay system in accordance with embodiments consistent with the present invention. In some embodiments, the method includes the steps of providing a sample including a biomolecule to be analyzed from a service requester to a service provider and the service requester receiving analytical results from the service provider, wherein the results are produced using a device provided by the invention. In some embodiments, the method is performed for remunerative consideration, e.g., fee-for-service or contract service agreements. In addition, the sample may be shipped directly between the service requester and the service provider, or mediated by a vendor. In some embodiments, the service provider or vendor may be geographically located in a territory outside of the United States of America, e.g. in another country.

For all patents, applications, or other reference cited herein, it should be understood that it is incorporated by reference in its entirety for all purposes as well as for the proposition that is recited. Where any conflict exits between a document incorporated by reference and the present application, this application will dominate.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will suppercede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

EXAMPLES

Example 1

Construction of a High Throughput Bioassay System

Hereinafter, a method for manufacturing a bioassay system 1 will be described in detail by referring to FIGS. 1-4. First, a silicon substrate 10 is provided with a plurality of light detectors 210 formed on an upper surface of substrate 10 by commercially available 0.25 micro-meter semiconductor manufacturing process for general logic and optical devices. Light detectors 210 are photodiode photon detectors, each having a diameter of 24 μm and an exposure area of 452 μm$^2$. Each light detector is arranged adjacent to each other, such that an array of 512 columns and 512 rows of light detectors 210 is formed on substrate 10.

A plurality of control circuits 215 is formed on the upper surface of substrate 10 where light detectors 210 are not formed. In this embodiment, one control circuit 215 corresponds to one light detector 210, so as to control the operation of its corresponding light detectors 210 and to control the communication between light detectors 210 and detection and recordation system 2.

In this embodiment, a filter layer 240 is formed over the upper surface of light detectors 210 and control circuits 215. Global planarization process is applied to the upper surface of light detectors 210 and control circuits 215 before forming filter layer 240. Filter layer 240 includes a plurality of sublayers. In this embodiment, filter layer 240 is formed by first depositing a sublayer having a higher refractive index over the planarized upper surface of light detectors 210 and control circuits 215. Then, a sublayer having a lower refractive index is deposited on the sublayer having a higher refractive index already formed. By continuously depositing sublayers of higher refractive indices and lower refractive indices, filter layer 240 is formed until a large number of sublayers has been so deposited. In this embodiment, filter layer 240 includes a hundred and one sublayers.

Referring to FIG. 5, there is illustrated a table for summarizing an example construction of filter layer 240. In FIG. 5, a lower numbered sublayer denotes a sublayer closer to the bottom surface of filter layer 240 and a higher number sublayer denotes a sublayer closer to the upper surface of filter layer 240. As shown in FIG. 5, in this particular embodiment, odd numbered sublayers of filter layer 240 are made of, for example, Niobium Oxide ($Nb_2O_5$), which has a higher refractive index. Even numbered sublayers are made of, for example, Silicon Oxide ($SiO_2$), which has lower refractive index. The sublayers may be formed by using a sputtering system, an example of which includes Model No. RAS 1100 of Radical Assisted Sputtering Series, manufactured by Shincron Co., Ltd. (Shinagawa-ku, Tokyo, JAPAN). The thickness of each sublayer in this example is also provided in the table of FIG. 5. The resultant filter layer 240 is highly transparent with respect to the fluorescent light of fluorophore Cy5 and has a low transparency with respect to the light emitted from Helium-Neon laser at a wavelength of about 633 nm, which is used as an external light source to excite fluorophore Cy5.

Referring back to FIGS. 2 and 4, blind sheet 230 having pinhole 235 is formed on filter layer 240. Hereinafter, a process for fabricating blind sheet 230 having pinhole 235 over filter layer 240 or substrate 10 will be described in detail.

First, a photoresist layer is formed on filter layer 240 (if filter layer 240 is optionally formed on the upper surface of light detectors 210 and control circuits 215) or on the planarized upper surface of light detectors 210 and control circuits 215 (if filter layer 240 is not formed) by, for example, spin coating a resist material on filter layer 240. Thereafter, the photoresist layer is developed to form a photoresist pattern at pinhole regions. The photoresist pattern is formed by covering the pinhole regions using a photomask, and exposing the photoresist layer such that only the regions covered by the photomask remain on filter layer 240 or the planarized upper surface of light detectors 210 and control circuits 215.

Then, a metal layer is deposited over filter layer 240 where the photoresist pattern has been formed. In this embodiment, the metal layer comprises chromium (Cr), which is deposited over filter layer 240 or the planarized upper surface of light detectors 210 and control circuits 215 by performing a magnetron sputtering process.

Subsequently, a portion of the metal layer on the pinhole regions and the photoresist pattern in the pinhole regions are removed, thereby forming blind sheet 230 with pinholes 235.

Alternatively, blind sheet 230 may be formed by first depositing a metal layer (e.g., Cr) on filter layer 240, and then forming a mask on the metal layer, thereby exposing portions of an upper surface of the metal layer. The exposed portions of the metal layer are then etched until filter layer 240 is exposed, thereby forming pinholes on the metal layer. Then, the mask is removed from the metal layer and blind sheet 230 having pinholes 235 is formed on filter layer 240.

Referring again to FIGS. 2 and 4, in this embodiment, linker site 220 is formed by filling a supporting material into pinhole 235 or cavity 450. The supporting material may be polymers or inorganic materials transparent to the fluorescent light emitted from fluorophore 36.

Referring again to FIG. 1, although only twelve optical detection apparatuses 20 are illustrated. It is appreciated that at least ten thousand optical detection apparatuses 20 can be formed on substrate 10. For example, in this embodiment, each optical detection apparatus 20 has a circular shape with a radius of about 5 μm or less, which may occupy an area of about 100 μm$^2$. For a substrate 10 having an area of 1 inch$^2$, (i.e., 2.54 cm by 2.54 cm), it is possible to construct more than six million optical detection apparatuses 20 on one substrate 10. By simultaneously operating those six million optical detection apparatuses 20, the biomolecules can be detected with high throughput.

Example 2

Attachment and Detection of Biomolecules with High Throughput Bioassay System

A fluorescent dye Cy5 labeled nucleic acid is used to test the detection system. Cy5 and biotin are affixed to the 3' and 5' ends, respectively, of a 60-mer oligonucleotide. The labeled and biotinylated DNA is dissolved in TrisMg (10 mM Tris, 10 mM NaCl, 100 mM $MgCl_2$, pH 8.0) buffer, deposited on the address array, and incubated in humid chamber. After about 30 minutes, unbound DNA is washed off with Tris buffer.

Excitation light is provided via a 635 nm light emitting diode, which may be formed on a blind sheet. To read the signal from each pixel, excitation light is on for about 1-5 seconds, the signal is recorded from each pixel, and the cycle is repeated for 100 runs. Representative average signals and corresponding standard deviations of each pixel are then calculated accordingly. Signals before and after DNA sample deposition are compared and pixels with an average signal difference greater than 3 times of sum of the standard deviations are considered positive pixels, i.e. $(Avg_{After} - Avg_{Before}) > 3 \times (STD_{After} + STD_{Before})$.

Example 3

Linking Quantum Dot to Polymerase

Below are two methods that conjugate functionalized quantum dots to primary amines on a polymerase molecule. The first uses amine-activated dots, the second uses carboxyl-activated dots.

3.1. Conjugation of Amine EVITAG™ to DNA Polymerase

Amine EVITAG™ (ex. Evident Technologies, cat# E2-C11-AM2-0620; the EVITAG™ suite of QD products are also sold under the eFluor™ mark by eBioscience, Inc., San Diego, Calif.) functionalized quantum dots (QDs) are activated by BS3 (Bis-(sulfosuccinimidyl) suberate), a homobifunctional, water-soluble crosslinker, which contains an amine-reactive N-hydroxysulfosuccinimide (NHS) ester at each end of an 8-carbon spacer arm. NHS esters react with primary amines on the surface of QDs at pH 7-9 to form stable amide bonds, and release the N-hydroxysulfosuccinimide leaving group. Taq DNA Polymerase or Phi29 DNA Polymerase have several primary amines (e.g., lysine (K) residues and the N-terminus of each polypeptide) that are available as targets for NHS-ester crosslinking.

3.1.1. Surface Activation of Quantum Dot

Activate 2.0 nmol of EVITAG™ with 25 µL 10 mM BS3 (Bis(sulfosuccinimidyl) suberate, Pierce, part #21580) and 25 µL 10×PBS (Phosphate buffer saline, pH 7.4) in a final volume to 250 µL with dH2O. After incubating for 30 minutes, the solution is desalted using a PD-10 column (Amersham Biosciences, product code 17-0851-01), and eluted with 1×PBS. The colored portion contains activated QDs.

3.1.2. DNA Polymerase Coupling

Polymerase is coupled by adding 100 µg of DNA polymerase in 0.1 M Sodium carbonate buffer, pH 9.2 to the mixture. After mixing well, the sample is incubated at 4° C. with tilt rotation for 2 hours.

3.1.3. Purification of QD-Conjugated Polymerase

The conjugate is concentrated to a total volume of ~200 µl by centrifugation with 30K Microspin filter (Pall Corporation, part # OD100C33) at 6,000 rpm for 5-10 minutes. The conjugate is washed over the 30K MicroSpin filter twice with dH2O.

Next, the conjugate is purified by size exclusion over Superdex 30/75 Resin (GE Healthcare, part # 17-0905-10 or 17-1044-10 for small proteins and peptides). The column is pre-equilibrated with dH2O before loading the concentrated coupling mix onto the column and allowing it to enter the column bed. The samples are eluted under blacklight excitation with dH2O and the fluorescent fractions are collected. The fluorescent fractions are pooled and concentrated to a total volume of ~100 µl by centrifugation with a 100K Microspin filter at 6,000 rpm for 5-10 minutes. The purified and concentrated conjugate may be stored at 4° C.

3.2. Conjugation of Carboxyl EVITAG™ to DNA Polymerase

Carboxyl EVITAG™ (ex. Evident Technologies, cat# E2-C11-CB2-0620) functionalized QDs are activated via EDC-mediated Sulfo-NHS ester coupling reactions. The amine-reactive Sulfo-NHS ester react with primary amines in the side chain of lysine (K) residues on, e.g., Taq DNA Polymerase or Phi29 DNA Polymerase.

3.2.1. Surface Activation of Quantum Dot 2.0 nmol of EVITAG™ are diluted in 25 mM MES pH 5.0 buffer. Immediately before use, EDC (1-Ethyl-3-[3-dimethylaminopropyl]carbodiimide Hydrochloride, Pierce, part #22980) is dissolved in cold 25 mM MES pH 5.0 to a concentration of 50 mg/ml. In parallel, 50 mg/ml solution of Sulfo-NHS (Pierce, part # 24525) in 25 mM MES, pH 5.0 are prepared similarly.

Next, 50 µl of EDC solution and 50 µl of Sulfo-NHS solution are added to the EVITAG™ solution. The mixture is mixed well and incubated with slow tilt rotation at room temperature for 30 minutes. The mixture is then desalted using a PD-10 column (Amersham Biosciences, product code 17-0851-01), eluting with 0.1 M Sodium carbonate buffer, pH 9.2. The colored portion containing the activated QDs is collected.

3.2.2. DNA Polymerase Coupling

Add 100 µg of DNA Polymerase in 0.1M Sodium carbonate buffer, pH 9.2 is added to the mixture. After mixing well, the sample is incubated at 4° C. with tilt rotation for 2 hours.

3.2.3. Purification of QD-Conjugated Polymerase

The conjugate is concentrated to a total volume of ~200 µl by centrifugation with 30K Microspin filter (Pall Corporation, part # OD100C33) at 6,000 rpm for 5-10 minutes. The conjugated is washed over the 30K MicroSpin filter twice with dH2O, Next, the conjugate is purified by size exclusion with Superdex 30/75 Resin.

Briefly, the column is pre-equilibrated with dH2O. The concentrated coupling mix is then loaded onto the column and allowed to enter the column bed. The column is eluted under blacklight excitation with dH2O and the fluorescent fractions are collected. Fluorescent fractions are pooled and concentrated to a total volume of ~100 µl by centrifugation with 100K Microspin filter at 6,000 rpm for 5-10 minutes.

The purified and concentrated conjugate may be stored at 4° C.

Example 4

Linking Polymerase to the Device

Two methods of using a photoNHS (N-hydroxy succinimido carboxylate molecule linked to a azidonitrobenzene molecule with a carbon chain linker) to attach an enzyme, e.g., polymerase, to a device are described.

4.1. UV Surface Activation

A photoNHS is used to attach a polymerase to an amine-modified surface on the apparatus by photoactivation with the UV light. UV light excites the azidonitrobenzene moiety to produce a highly reactive nitrene group by eliminating nitrogen. Nitrene reacts with $NH_2$ on the surface of the device and forms a hydrazine bond. The other end of the linker is NHS carboxylate, which reacts with lysine residues on the polymerase to produce an amide covalent bond.

4.1.1. Surface Preparation

A solution of 1 mM photoNHS (Sigma, Art No. A3407, molecular weight 390.35) is prepared in 95% ethanol. The amine-modified surface is washed with carbonate buffer (pH 9.3) and then 95% ethanol. Next, the photoNHS solution is applied to the amine-modified surface. 254~365 nm UV light is shone on the surface for 3 minutes, followed by three 95% ethanol rinses.

4.1.2. End-cap of the Amine

A solution of 10 mM N-acetoxysuccinimide is prepared in carbonate buffer (pH 9.3) and applied to the surface to end-cap any un-reacted amines. The apparatus is incubated at room temperature for two hours with gentle shaking. Next the surface is washed three times each with carbonate buffer and distilled, deionized water.

4.1.3. DNA Polymerase Coupling

Next, a solution of 1 mM DNA Polymerase in carbonate buffer (pH 9.3) is applied to the surface and incubated at room temperature for two hours under continuous gentle shaking. The surface is then washed three times each with carbonate buffer and pH 7.4 PBS (phosphate buffered saline). The polymerase-bonded surface may be stored at 4° C.

4.2. Buffered Surface Activation

In another embodiment, the photoNHS can be activated and conjugated to the surface under buffered conditions. UV light is then used to activate aazidonitrobenzene moiety in the presence of polymerase. Again, highly reactive nitrene is formed under UV light as an electron deficient group and readily reacts with primary amines on the surface of a polymerase, forming a covalent bond to the surface.

4.2.1. Surface Preparation

A solution of 1 mM photoNHS (Sigma, Art No. A3407, molecular weight 390.35) is prepared in carbonate buffer (pH 9.3). An amine-modified surface is rinsed with carbonate buffer (pH 9.3). The photoNHS solution is applied to the amine-modified surface and incubated for two hours under continuous, gentle shaking. The surface is then rinsed three times with carbonate buffer.

4.2.2. End-cap of the Amine

A 10 mM N-acetoxysuccinimide solution prepared in carbonate buffer (pH 9.3) is applied to the surface to end-cap the un-reacted amine group. The solution is incubated at room temperature for 2 hours under continuous, gentle shaking and then rinsed three times with PBS buffer (pH 7.4).

4.2.3. DNA Polymerase Coupling

A solution of 1 mM DNA Polymerase is prepared in PBS buffer (pH 7.4) and applied to the end-capped surface. UV light (254~365 nm) is shone on the surface for 3 minutes. Next the surface is rinsed with PBS (pH 7.4) three times. The polymerase-bonded surface can then be stored at 4° C.

Example 5

Base Extension Sequencing Modalities

As discussed above, there are two general ways to recognize the nucleotide added during stepwise extension: sequentially adding four identically-labeled nucleotides or simultaneously adding four differentially-labeled nucleotides. Example of each of these modalities are provided below.

5.1 Four Nucleotides with Identical Labels are Added Sequentially 5.1.1 Adenine (A) molecule extension: Add blocked and labeled adenine and suitable polymerase into a sequencing reaction buffer solution (e.g., 40 mM Tris-HCl pH 9, 1 mM $MgCl_2$). Adenine will be added to the 3'-end of the sequencing primer only when thymine (T) is the nucleotide in the nucleic acid being sequenced is adjacent to the 5'-end of the end link primer. If the nucleotide of the nucleic acid closest to the 3'-end of the primer is guanine (G), cytosine (C), or adenine (A), then no extension will occur.

5.1.2 Extension reaction cleaning step: After the extension reaction is completed, the array chip is washed once using 5×SSC and 0.1% SDS, and once using 5×SSC, to remove the adenine and unreacted solution 5.1.3 Fluorescent detection and recordation: Read the fluorescent signal at the linker site to determine whether an adenine was extended, which indicates a corresponding thymine in the nucleic acid being sequenced.

5.1.4 Remove protection and fluorescent groups: After detection, the protection and fluorescent groups are removed by chemical or enzymatic cleavage.

5.1.5 Cleaning step: The array chip is washed once with 5×SSC and 0.1% SDS, and once with 5×SSC, to remove the cleaved protection and labeling groups.

5.1.6 Proofreading and recordation: Confirm the successful removal of the protection and fluorescent groups from the previous extension step. If there are residual protection and fluorescent groups, the detection and analysis software on, for example, detection and recordation system 2 will record the location. The recordation of the sequencing reaction can proceed only if removal of the protection and fluorescent groups is confirmed in the next cleaning step.

5.1.7 Repeat 5.1.1-5.1.6, this time, using guanine for the extension reaction.

5.1.8 Repeat 5.1.1-5.1.6, this time, using cytosine for the extension reaction.

5.1.9 Repeat 5.1.1-5.1.6, this time, using thymine for the extension reaction.

5.1.10 Every four extension reactions using A, G, C, T is a cycle. By repeating the cycle, the sequence of a nucleic acid is determined in a stepwise fashion.

5.2. Four Nucleotides with Distinct Labels are Added Simultaneously 5.2.1 Base extension reaction: The four blocked and distinctly labeled DNA nucleotides (A, G, C, T) and nucleic acid polymerase are added to a sequencing buffer on the array. The extension reaction can only occur at the 3'-end of the sequencing primer. The nucleotide complementary to the nucleotide of the nucleic acid being sequenced closest to the 5'-end of the linking primer will be added to the 3'-end of sequencing the primer, see, e.g., FIG. 6.

5.2.2 Extension reaction cleaning step: After the extension reaction is completed, the chip is washed once with 5×SSC and 0.1% SDS, and once with 5×SSC, to remove residual materials in the reaction solution.

5.2.3 Fluorescent detection and recordation: Detect each of the distinct fluorescent signals at each linker site to determine the nucleotide added.

5.2.4 Remove the protection and fluorescent groups: After detection, the protection and fluorescent groups are removed by chemical or enzymatic cleavage.

5.2.5 Cleaning step: The chip is washed once with 5×SSC and 0.1% SDS, and once with 5×SSC, to remove the cleaved protection and fluorescent groups.

5.2.6 Proof reading and recordation: Confirm the successful removal of the protection and fluorescent groups from the previous step. If there are residual protection group and fluorescent groups, the detection and analysis software on, for example, detection and recordation system 2 will record the location. The recordation of the sequencing reaction can proceed only if the removal of the protection group and fluorescent groups at the location is confirmed in the next cleaning step.

5.2.7 Repeat 5.2.1-5.2.6. Repeat the reaction cycle, to determine the sequence of the nucleic acid.

Example 6

Sequencing of a Known Nucleic Acid

A chemically synthesized 60mer oligonucleotide, with known sequence: biotin-5'-tcag tcag tcag tcag tcag tcag tcag tcag tcag tcag tc ACACGGAGGTTCTA-3', serves as a sequencing template. The sequencing template is combined with a 14mer oligonucleotide sequencing primer (5'-TAGMCCTCCGTGT-3'). The 5'-end of the template is modified to include a biotin molecule. The template molecule is affixed to a reactor surface containing streptavidin. The sequencing reaction uses a DNA polymerase to perform a base-extension reaction in a 1×Sequencing buffer with 15 mM DTT. Each extension reaction step adds only one type of nucleotide which has a secondary extension protection (blocking) group and a fluorescent label (e.g., Cy5). If the nucleotide of the DNA template adjacent to the 3'-end of the sequencing primer is complementary to the added nucleotide, the fluorescently labeled base is then added. After washing off unreacted base materials, the fluorescent signal is detected. If the added base is not complementary, no fluorescent signals will be detected. After detection, the protection fluorescent groups are removed chemically, and the array is further washed using a salt containing solution (e.g., 5×SSC; 0.1% SDS), and detected once again to confirm removal of fluorescent label. For locations where no fluorescent signals are detected after the removal and washing steps, it is regarded that the fluorescent label has been removed. The fluorescent signal obtained in the next reaction cycle is then regarded as the signal of the next extended sequenced. For the locations where fluorescent signals still remain after removal and washing, the location is recorded as having an incomplete removal reaction using software. The signal from the location can continue to be recorded only if the removal step in the next cycle is confirmed. Based on this method, one can sequentially add the four types of reaction base materials and perform the reactions cyclically. Accordingly, the sequence of the template is determined.

Other embodiments consistent with the present invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for identifying a single biomolecule, comprising:
   a substrate having a light detector; and
   a linker site formed over the light detector, the linker site being treated to affix the biomolecule to the linker site;
   wherein the linker site is proximate to the light detector and is spaced apart from the light detector by a distance of less than or equal to 100 micrometers.

2. The apparatus of claim 1, further comprising a blind sheet formed over the substrate, the blind sheet including a pinhole having a diameter, wherein the linker site is formed proximate to the pinhole.

3. The apparatus of claim 2, wherein the pinhole has a diameter of less than or equal to 1,000 nanometers.

4. The apparatus of claim 2, wherein the pinhole has a diameter of less than or equal to 200 nanometers.

5. The apparatus of claim 2, further comprising a filter layer formed between the substrate and the blind sheet.

6. The apparatus of claim 2, further comprising a microlens formed between the substrate and the blind sheet.

7. The apparatus of claim 1, wherein the distance is less than or equal to 25 micrometers.

8. The apparatus of claim 1, wherein the distance is less than or equal to 6 micrometers.

9. The apparatus of claim 1, wherein the light detector collects light from the biomolecule within a solid angle, the solid angle being greater than or equal to 0.8 SI steridian.

10. An optical detection system, comprising at least 10,000 apparatuses as recited in claim 1.

11. A method of sequencing a plurality of nucleic acid molecules, the method comprising the steps of:
    affixing a plurality of nucleic acid molecules to the linker sites of the optical detection system of claim 10; and
    performing nucleic acid sequencing of the nucleic acid molecules in parallel on the optical detection system.

12. A method of detecting a plurality of biomolecules, the method comprising the steps of:
    affixing a plurality of biomolecules to the linker sites of the optical detection system of claim 10; and
    detecting the biomolecules on the optical detection system in parallel.

13. An optical detection system, comprising at least 250,000 apparatuses as recited in claim 1.

14. An optical detection system, comprising at least 2,000,000 apparatuses as recited in claim 1.

15. An optical detection system, comprising at least 10,000,000 apparatuses as recited in claim 1.

16. A method of sequencing a nucleic acid, comprising the steps of:
    affixing one nucleic acid molecule to the linker site of the apparatus of claim 1; and
    performing nucleic acid sequencing of the nucleic acid molecule on the apparatus.

17. The method of claim 16, wherein the nucleic acid is affixed to the linker site by binding to a polymerase molecule affixed to the linker site.

18. The method of claim 16, wherein the nucleic acid sequencing comprises the step of adding labeled nucleotides to the apparatus.

19. The method of claim 18, wherein the nucleotides are labeled fluorescently.

20. The method of claim 19, wherein the nucleotides are labeled fluorescently on their terminal phosphate.

21. The method of claim 16, wherein the nucleic acid sequencing is base extension sequencing and includes the step of adding blocked and labeled nucleotides to the apparatus.

22. The method of claim 21, wherein the nucleotides are labeled fluorescently.

23. The method of claim 22, wherein the nucleotides have identical fluorescent labels and are added sequentially.

24. The method of claim 22, wherein the nucleotides have distinct fluorescent labels and are added simultaneously.

25. The method of claim 16, wherein the nucleic acid sequencing is a ligase-based sequencing.

26. The method of claim 16, wherein the nucleic acid is amplified at the linker site before nucleic acid sequencing.

27. The method of claim 16, wherein the sequence of the nucleic acid is unknown.

28. The method of claim 16, wherein the nucleic acid is detected with a label excited by Förster resonance energy transfer (FRET).

29. The method of claim 16, wherein the nucleic acid is detected with a label by time-resolved fluorescence technology.

30. A method of detecting a biomolecule, comprising the steps of:
affixing one or more biomolecule to the linker site of the apparatus of claim 1; and
detecting the biomolecule on the apparatus.

31. The method of claim 30, wherein the biomolecule comprises a label.

32. The method of claim 31, wherein the label is fluorescent.

33. The method of claim 32, wherein the biomolecule comprises a moiety chosen from a polypeptide, antibody, lipid, vitamin, low molecular weight organic molecule, and polysaccharide.

34. The method of claim 33, wherein the biomolecule is affixed to the linker site of the apparatus by a linking molecule.

35. The method of claim 34, wherein the linking molecule comprises a capture molecule.

36. The method of claim 35, wherein the capture molecule is a protein.

37. The method of claim 35, wherein the capture molecule is an antibody.

38. The method of claim 35, wherein the linking molecule comprises a nucleic acid tag.

39. The method of claim 38, further comprising the step of detecting the nucleic acid tag of the linking molecule on the apparatus.

40. The method of claim 39, wherein the nucleic acid tag is detected by nucleic acid sequencing.

41. The method of claim 39, wherein the nucleic acid tag is detected by hybridization to a nucleic acid probe.

42. The method of claim 41, wherein the nucleic acid probe is labeled fluorescently.

43. A method of providing biomolecule analysis service, comprising the steps of:
providing a sample comprising a biomolecule from a service requester to a service provider;
the service requester receiving analytical results from the service provider, wherein the results are produced using the apparatus of claim 1.

44. The method of claim 43, wherein the method is performed for remunerative consideration.

45. The method of claim 44, wherein the service requester and the service provider are mediated by a vendor.

46. The method of claim 43, wherein the analytical results are produced in another country.

47. The method of claim 43, wherein the analytical results are produced in a country other than the United States of America.

48. An apparatus for identifying a single biomolecule, comprising:
a substrate having a light detector;
a linker site formed over the light detector, the linker site being treated to affix the biomolecule to the linker site; and
an excitation light source formed over the substrate;
wherein the linker site is proximate to the light detector and is spaced apart from the light detector by a distance of less than or equal to 100 micrometers.

49. The apparatus of claim 48, wherein the excitation light source includes a light emitting layer, the light emitting layer emitting excitation light to the linker site along a horizontal direction parallel to a surface of the light detector.

50. The apparatus of claim 49, further comprising a filter layer formed between the substrate and the light emitting layer.

51. The apparatus of claim 48, wherein the excitation light source is chosen from a light emitting diode (LED), an organic light emitting diode (OLED), a polymer light emitting diode (PLED), and a laser diode (LD).

52. The apparatus of claim 48, wherein the excitation light source provides excitation light of a first wavelength range not overlapping with a second wavelength range of light emitted from the biomolecule.

53. An apparatus for identifying a single biomolecule, comprising:
a substrate having a light detector; and
a linker site formed over the light detector, the linker site being treated to affix the biomolecule to the linker site;
wherein the light detector collects light emitted from the biomolecule within a solid angle of greater than or equal to 0.8 SI steridian.

54. An apparatus for identifying a single biomolecule, comprising:
a substrate having a light detector;
a linker site formed over the light detector, the linker site being treated to affix the biomolecule to it; and
an excitation light source formed over the substrate;
wherein the light detector collects light emitted from the biomolecule within a solid angle of greater than or equal to 0.8 SI steridian.

55. A method for manufacturing an apparatus for identifying a single biomolecule, comprising:
forming a light detector and a control circuit on a substrate;
forming a blind sheet having a pinhole over the substrate; and
forming a linker site over the light detector and proximate to the pinhole, the linker site being treated to affix the biomolecule to the linker site, wherein the linker site is proximate to the light detector and is spaced apart from the light detector by a distance of less than or equal to 100 micrometers.

56. The method of claim 55, further comprising forming a filter layer between the substrate and the blind sheet.

57. The method of claim 56, wherein forming the blind sheet comprises:
- forming an opaque layer on the filter layer;
- forming a photoresist layer on the opaque layer;
- patterning the photoresist layer to expose a portion of the opaque layer;
- etching the opaque layer using the patterned photoresist layer as a mask until the filter layer is exposed; and
- removing the photoresist layer.

58. The method of claim 57, wherein the opaque layer comprises metal.

* * * * *